US011441124B2

(12) United States Patent
Yivgi-Ohana et al.

(10) Patent No.: US 11,441,124 B2
(45) Date of Patent: Sep. 13, 2022

(54) MAMMALIAN CELLS ENRICHED WITH FUNCTIONAL MITOCHONDRIA

(71) Applicant: MINOVIA THERAPEUTICS LTD., Rehovot (IL)

(72) Inventors: Natalie Yivgi-Ohana, Haifa (IL); Uriel Halavee, Tel Aviv (IL)

(73) Assignee: Minovia Therapeutics Ltd., Rehovot (IL)

( * ) Notice: Subject to any disclaimer, the term of this patent is extended or adjusted under 35 U.S.C. 154(b) by 57 days.

(21) Appl. No.: 16/445,680

(22) Filed: Jun. 19, 2019

(65) Prior Publication Data
US 2019/0330595 A1    Oct. 31, 2019

Related U.S. Application Data

(63) Continuation of application No. 15/551,600, filed as application No. PCT/IL2016/050205 on Feb. 24, 2016, now abandoned.

(60) Provisional application No. 62/120,907, filed on Feb. 26, 2015.

(51) Int. Cl.
| | |
|---|---|
| *C12N 5/077* | (2010.01) |
| *A61K 35/28* | (2015.01) |
| *C12N 5/071* | (2010.01) |
| *C12N 5/12* | (2006.01) |

(52) U.S. Cl.
CPC ............ *C12N 5/0669* (2013.01); *A61K 35/28* (2013.01); *C12N 5/067* (2013.01); *C12N 5/0656* (2013.01); *C12N 5/12* (2013.01)

(58) Field of Classification Search
None
See application file for complete search history.

(56) References Cited

U.S. PATENT DOCUMENTS

| | | | |
|---|---|---|---|
| 7,279,326 B2 | 10/2007 | Weissig | |
| 7,407,800 B1 | 8/2008 | Benton | |
| 2005/0153381 A1* | 7/2005 | Marusich | G01N 33/573 435/7.92 |
| 2010/0278790 A1 | 11/2010 | Prockop | |
| 2011/0008310 A1 | 1/2011 | Cataldo | |
| 2011/0105359 A1 | 5/2011 | Czerwinski | |
| 2012/0058091 A1 | 3/2012 | Rogers | |
| 2012/0107285 A1 | 5/2012 | Hyde | |
| 2013/0022666 A1 | 1/2013 | Brezezinska | |
| 2013/0034527 A1* | 2/2013 | Hyde | G16B 99/00 424/93.21 |
| 2013/0149778 A1 | 6/2013 | Chang et al. | |
| 2015/0374736 A1* | 12/2015 | Lee | A61K 38/193 424/85.1 |

FOREIGN PATENT DOCUMENTS

| | | | |
|---|---|---|---|
| WO | 2004100773 A2 | 11/2004 | |
| WO | 2008137035 A1 | 11/2008 | |
| WO | 2008152640 A2 | 12/2008 | |
| WO | 2013002880 A1 | 1/2013 | |
| WO | 2013035101 A1 | 3/2013 | |
| WO | 2013171752 A1 | 11/2013 | |
| WO | WO 2016/008937 A1 | 7/2015 | |
| WO | 2016008937 A1 | 1/2016 | |
| WO | WO-2016008937 A1 * | 1/2016 | ............... C12N 5/00 |

OTHER PUBLICATIONS

Sidney et al. "Concise review: evidence for CD34 as a common marker for diverse progenitors." Stem Cells 32.6 (2014): 1380-1389. (Year: 2014).*
Yasuda et al., (2011) Tunneling nanotubes mediate rescue of prematurely senescent endothelial cells by endothelial progenitors: exchange of lysosomal pool. Aging (Albany NY) 3(6): 597-608.
Yu et al., (2007) Induced pluripotent stem cell lines derived from human somatic cells. science, 318(5858), 1917-1920.
Abramova et al., (1979) Injection of mitochondria into oocytes and fertilized eggs. Ontogenez 10(4): 401-5. Abstract.
Abramova et al., (1983) Regulation of the number and function of mitochondria during artificial increase of their mass in fish embryos. Biokhimiia 48(8): 1279-86. Abstract.
Abramova et al., (1989) The functioning of mammalian mitochondria injected into fish embryos. Ontogenez 20(3): 320-3. Abstract.
Bourgeron et al., (1992) Isolation and characterization of mitochondria from human B lymphoblastoid cell lines. Biochem Biophys Res Commun 186(1): 16-23.
Caicedo et al., (2015) MitoCeption as a new tool to assess the effects of mesenchymal stem/stromal cell mitochondria on cancer cell metabolism and function. Sci Rep 5: 9073; 10 pages.
Cárdenes et al., (2013) Mesenchymal stem cells: a promising therapy for the acute respiratory distress syndrome. Respiration 85(4): 267-278.
Chen et al., (2010) Generation of retinal ganglion-like cells from reprogrammed mouse fibroblasts. Investigative ophthalmology & visual science, 51(11), 5970-5978.
Choi et al., (2005) Analysis of proteome bound to D-loop region of mitochondrial DNA by DNA-linked affinity chromatography and reverse-phase liquid chromatography/tandem mass spectrometry. Ann N Y Acad Sci 1042: 88-100.
Clark and Shay (1982) Mitochondrial transformation of mammalian cells. Nature 295(5850): 605-7.
Cook et al., (1983) Structural changes of isolated hepatocytes during treatment with digitonin. Biochimica et Biophysica Acta (BBA)—Molecular Cell Research, 763(4), 356-367.
Csordás (2006) Mitochondrial transfer between eukaryotic animal cells and its physiologic role. Rejuvenation Res 9(4): 450-4.
Das Neves et al., (2010) Connecting variability in global transcription rate to mitochondrial variability. PLoS biology, 8(12), e1000560.
Frazier et al., (2006) Mitochondrial morphology and distribution in mammalian cells. Biol Chem 387(12): 1551-8.

(Continued)

*Primary Examiner* — Emily A Cordas
(74) *Attorney, Agent, or Firm* — DLA Piper LLP (US)

(57) ABSTRACT

The present invention provides human bone-marrow cells enriched with functional mitochondria, methods for their production, and therapeutic methods utilizing such cells.

14 Claims, 10 Drawing Sheets

(56) References Cited

OTHER PUBLICATIONS

Gasnier et al., (1993) Use of Percoll gradients for isolation of human placenta mitochondria suitable for investigating outer membrane proteins. Anal Biochem 212(1): 173-8.

Gavazza et al., (2005) Sensitivity of mitochondria isolated from liver and kidney of rat and bovine to lipid peroxidation: a comparative study of light emission and fatty acid profiles. Mol Cell Biochem 280(1-2): 77-8.

Griffiths and Rutter (2009) Mitochondrial calcium as a key regulator of mitochondrial ATP production in mammalian cells. Biochim Biophys Acta 1787(11): 1324-33.

Guantes et al., (2016) Mitochondria and the non-genetic origins of cell-to-cell variability: More is different. BioEssays, 38(1), 64-76.

Hartwig et al., (2009) A critical comparison between two classical and a kit-based method for mitochondria isolation. Proteomics 9(11): 3209-14.

Islam et al., (2012) Mitochondrial transfer from bone-marrow-derived stromal cells to pulmonary alveoli protects against acute lung injury. Nature medicine, 18(5), 759-765.

Jenuth et al., (1996) Random genetic drift in the female germline explains the rapid segregation of mammalian mitochondrial DNA. Nat Genet, 14(2):146-51.

Jenuth et al., (1997) Tissue-specific selection for different mtDNA genotypes in heteroplasmic mice. Nature genetics, 16(1), 93-95.

Katrangi et al., (2007) Xenogenic transfer of isolated murine mitochondria into human rho0 cells can improve respiratory function. Rejuvenation Res 10(4): 561-70.

King and Attardi (1988) Injection of mitochondria into human cells leads to a rapid replacement of the endogenous mitochondrial DNA. Cell 52(6): 811-9.

Kitani et al., (2014) Direct human mitochondrial transfer: a novel concept based on the endosymbiotic theory. Transplant Proc 46(4): 1233-1236.

Kuznetsov et al., (2003) Cryopreservation of mitochondria and mitochondrial function in cardiac and skeletal muscle fibers. Anal Biochem 319(2): 296-303.

Larsen et al., (2012) Biomarkers of mitochondrial content in skeletal muscle of healthy young human subjects. The Journal of physiology, 590(14), 3349-3360.

Lin et al., (2012) Mouse mtDNA mutant model of Leber hereditary optic neuropathy. Proceedings of the National Academy of Sciences, 109(49), 20065-20070.

Martinez et al., (1997) Structural and functional changes in mitochondria associated with trophoblast differentiation: methods to isolate enriched preparations of syncytiotrophoblast mitochondria. Endocrinology 138(5): 2172-83.

McCully et al., (2009) Injection of isolated mitochondria during early reperfusion for cardioprotection. Am J Physiol Heart Circ Physiol 296(1): H94-H105.

Modica-Napolitano and Singh (2002) Mitochondria as targets for detection and treatment of cancer. Expert Rev Mol Med 4(9): 1-19.

Muir et al., (2016) Mitochondrial content is central to nuclear gene expression: Profound implications for human health. BioEssays, 38(2), 150-156.

Parone et al., (2008) Preventing mitochondrial fission impairs mitochondrial function and leads to loss of mitochondrial DNA. PLoS One 3(9): e3257.

Pasquier et al., (2013) Preferential transfer of mitochondria from endothelial to cancer cells through tunneling nanotubes modulates chemoresistance. Journal of translational medicine, 11(1), 94.

Pinkert et al., (1997) Mitochondria transfer into mouse ova by microinjection. Transgenic Res 6(6): 379-83.

Pipino et al., (2012) Placenta as a reservoir of stem cells: an underutilized resource? Br Med Bull, pp. 1-25.

Plotnikov et al., (2010) Cytoplasm and organelle transfer between mesenchymal multipotent stromal cells and renal tubular cells in co-culture. Exp Cell Res 316(15): 2447-55.

Romero-Moya et al., (2013) Cord blood-derived CD34+ hematopoietic cells with low mitochondrial mass are enriched in hematopoietic repopulating stem cell function. Haematologica, 98(7), 1022-1029.

Rousou et al., (2004) Opening of mitochondrial KATP channels enhances cardioprotection through the modulation of mitochondrial matrix volume, calcium accumulation, and respiration. Am J Physiol Heart Circ Physiol 287(5): H1967-76.

Shi et al., (2008) Liposome-mediated transfer of labeled mitochondria into cultured cells. Ethnicity and Disease 18(S1):43-44.

Sidney et al., (2014) Concise review: evidence for CD34 as a common marker for diverse progenitors. Stem Cells 32(6): 1380-1389.

Spees et al., (2006) Mitochondrial transfer between cells can rescue aerobic respiration. Proceedings of the National Academy of Sciences, 103(5), 1283-1288.

Szewczyk and Wojtczak (2002) Mitochondria as a pharmacological target. Pharmacol Rev 54(1): 101-27.

Takeda et al., (2005) Microinjection of cytoplasm or mitochondria derived from somatic cells affects parthenogenetic development of murine oocytes. Biol Reprod 72(6): 1397-40.

Tuckey (2005) Progesterone synthesis by the human placenta. Placenta 26(4): 273-81.

Tuckey and Sadleir (1999) The concentration of adrenodoxin reductase limits cytochrome p450scc activity in the human placenta. Eur J Biochem 263(2): 319-25.

Van Blerkom et al., (1998) Mitochondrial transfer between oocytes: potential applications of mitochondrial donation and the issue of heteroplasmy. Hum Reprod 13 (10): 2857-2868.

Wagle et al., (2011) The utility of an isolated mitochondrial fraction in the preparation of liposomes for the specific delivery of bioactives to mitochondria in live mammalian cells. Pharm Res 28(11): 2790-6.

Xu et al., (2012) Efficient commitment to functional CD34+ progenitor cells from human bone marrow mesenchymal stem-cell-derived induced pluripotent stem cells. PLoS One, 7(4), e34321.

Yamaguchi et al., (2007) Mitochondria frozen with trehalose retain a number of biological functions and preserve outer membrane integrity. Cell Death Differ 14(3): 616-24.

Frezza et al., "Organelle isolation: functional mitochondria from mouse liver, muscle and cultured fibroblasts", Nat. Protoc, 2007, 2(2):287-295.

Caicedo et al., "MitoCeption as a new tool to assess the effects metabolism and function", Scientific Reports, Mar. 2015, 5(1):1-10.

Chinnery et al., "The Challenges of Mitochondrial Replacement", PLOS Genetics, Apr. 2014, 10(4)1-2.

EP Office Action in European Application No. EP16754857.7, dated May 4, 2022, 10 pages.

Islam et al., "Mitochondrial transfer from bone-marrow-derived stromal cells to pulmonary alveoli protects against acute lung injury", Nature Medicine, Apr. 2012, 18(5):759-765.

Jacoby et al., "First-in-Human Mitochondrial Augmentation of Hematopoietic Stem Cells in Pearson Syndrome", Blood, American Society of Hematology, Nov. 2018, 132:1024.

Jacoby et al., "Mitochondrial augmentation of CD34+ cells from healthy donors and patients with mitochondrial DNA disorders conders functional benefit", NPJ Regenerative Medicine, Dec. 2021, 6(1):1-12.

Kitani et al., "Internalization of isolated functional mitochondria: involvement of macropinocytosis", J. Cell. Mol. Med., Apr. 2014, 18(8):1694-1703.

Pasquier et al., "Preferential transfer of mitochondria from endothelial to cancer cells through tunneling nanotubes modulates chemoresistance", J Transl Med, Apr. 2013, 11(94):1-14.

Spees et al., "Mitochondrial transfer between cells can rescue aerobic respiration", Proceedings of the National Academy of Sciences, Jan. 2006, 103(5):1283-1288.

Tachibana et al., "Mitochondrial Gene Replacement in Primate Offspring and Embryonic Stem Cells", Nature, Sep. 2009, 461(7262):367-372.

Tian et al., "Impaired Mitochondrial Function Results from Oxidative Stress in the Full-Term Placenta of Sows with Excessive Back-Fat", Animals, Feb. 2020, 10(360):1-19.

* cited by examiner

Bright Field + GFP     GFP

MAMMALIAN CELLS ENRICHED WITH FUNCTIONAL MITOCHONDRIA

RELATED APPLICATIONS

This application is a Continuation Application of U.S. application Ser. No. 15/551,600, filed Aug. 17, 2017, which is a National Phase Application of PCT/IL2016/050205, filed Feb. 24, 2016, which claims priority to U.S. Provisional Application No. 62/120,907, filed Feb. 26, 2015; the contents of all of which are incorporated herein by reference in their entirety.

FIELD OF THE INVENTION

The present invention relates to cells derived from human bone-marrow and enriched with functional mitochondria, methods for their production, and therapeutic methods utilizing such cells.

BACKGROUND OF THE INVENTION

The mitochondrion is a membrane bound organelle found in most eukaryotic cells, ranging from 0.5 to 1.0 μm in diameter. Mitochondria are found in nearly all eukaryotic cells and vary in number and location depending on the cell type. Mitochondria contain their own DNA (mtDNA) and their own machinery for synthesizing RNA and proteins. The mtDNA contains only 37 genes, thus most of the gene products in the mammalian body are encoded by nuclear DNA.

Mitochondria perform numerous essential tasks in the eukaryotic cell such as pyruvate oxidation, the Krebs cycle and metabolism of amino acids, fatty acids and steroids. However, the primary function of mitochondria is the generation of energy as adenosine triphosphate (ATP) by means of the electron-transport chain and the oxidative-phosphorylation system (the "respiratory chain"). Additional processes in which mitochondria are involved include heat production, storage of calcium ions, calcium signaling, programmed cell death (apoptosis) and cellular proliferation. Therefore, there are many diseases and disorders known in the art associated with malfunction or dysfunction of mitochondria which require treatment.

The ATP concentration inside the cell is typically 1-10 mM. ATP can be produced by redox reactions using simple and complex sugars (carbohydrates) or lipids as an energy source. For complex fuels to be synthesized into ATP, they first need to be broken down into smaller, simpler molecules. Complex carbohydrates are hydrolyzed into simple sugars, such as glucose and fructose. Fats (triglycerides) are metabolized to give fatty acids and glycerol.

The overall process of oxidizing glucose to carbon dioxide is known as cellular respiration and can produce about 30 molecules of ATP from a single molecule of glucose. ATP can be produced by a number of distinct cellular processes. The three main pathways used to generate energy in eukaryotic organisms are glycolysis and the citric acid cycle/oxidative phosphorylation, both components of cellular respiration, and beta-oxidation. The majority of this ATP production by a non-photosynthetic aerobic eukaryote takes place in the mitochondria, which can make up nearly 25% of the total volume of a typical cell.

Mitochondrial diseases are a group of disorders caused by dysfunctional mitochondria. Mitochondrial diseases may be caused by mutations in the mitochondrial DNA that affect mitochondrial function. Other causes of mitochondrial disease are mutations in genes of the nuclear DNA, whose gene products are imported into the Mitochondria (Mitochondrial proteins) as well as acquired mitochondrial conditions. Mitochondrial diseases take on unique characteristics both because of the way the diseases are often inherited and because mitochondria are so critical to cell function. The subclass of these diseases that have neuromuscular disease symptoms are often called a mitochondrial myopathy.

Mitochondrial disorders may be caused by mutations, acquired or inherited, in mitochondrial DNA (mtDNA) or in nuclear genes that code for mitochondrial components. They may also be the result of acquired mitochondrial dysfunction due to adverse effects of drugs, infections, or other environmental causes. Mitochondrial disease may become clinically apparent once the number of affected mitochondria reaches a certain level; this phenomenon is called "threshold expression". Mitochondrial DNA mutations occur frequently, due to the lack of error checking capability. This means that mitochondrial DNA disorders may occur spontaneously and relatively often. Defects in enzymes that control mitochondrial DNA replication (all of which are encoded for by genes in the nuclear DNA) may also cause mitochondrial DNA mutations. Most mitochondrial function and biogenesis is controlled by nuclear DNA. Human mitochondrial DNA encodes only 13 proteins of the respiratory chain, while most of the estimated 1,500 proteins and components targeted to mitochondria are nuclear-encoded. Defects in nuclear-encoded mitochondrial genes are associated with hundreds of clinical disease phenotypes including anemia, dementia, hypertension, lymphoma, retinopathy, seizures, and neurodevelopmental disorders.

Leber's hereditary optic neuropathy (LHON) or Leber optic atrophy is a mitochondrially inherited (transmitted from mother to offspring) degeneration of retinal ganglion cells (RGCs) and their axons that leads to an acute or sub-acute loss of central vision, affecting predominantly young adult males. However, LHON is only transmitted through the mother as it is primarily due to mutations in the mitochondrial (not nuclear) genome and only the egg contributes mitochondria to the embryo. LHON is usually due to one of three pathogenic mitochondrial DNA (mtDNA) point mutations. These mutations are at nucleotide positions 11778 G to A, 3460 G to A and 14484 T to C, respectively in the ND4, ND1 and ND6 subunit genes of complex I of the oxidative phosphorylation chain in mitochondria. These mutations can lead to the reduction in cellular energy production, which in turn results in cell damage and death of certain optic nerve cells. At this time, experts are unable to tell which, if any family members will develop symptoms, though on average 50% of men and 15% of women with a LHON mutation will lose vision in their lifetime.

Mitochondrial encephalomyopathy, lactic acidosis, and stroke-like episodes—abbreviated to MELAS—is one of the family of mitochondrial cytopathies, which also include MERRF, and Leber's hereditary optic neuropathy. The disease can manifest in both sexes. MELAS is caused by mutations in the genes in mitochondrial DNA. Some of the genes (MT-ND1, MT-ND5) affected in MELAS encode proteins that are part of NADH dehydrogenase (also called complex I) in mitochondria, that helps convert oxygen and simple sugars to energy. Other genes (MT-TH, MT-TL1, and MT-TV) encode mitochondrial specific transfer RNAs (tRNAs). Mutations in MT-TL1 cause more than 80% of all cases of MELAS. They impair the ability of mitochondria to make proteins, use oxygen, and produce energy.

WO 2013/002880 describes compositions and methods comprising bio-energetic agents for restoring the quality of aged oocytes, enhancing oogonial stem cells or improving derivatives thereof (e.g., cytoplasm or isolated mitochondria) for use in fertility-enhancing procedures.

WO 2013/035101 to the present inventors relates to mitochondrial compositions and therapeutic methods of using same, and discloses compositions of partially purified functional mitochondria and methods of using the compositions to treat conditions which benefit from increased mitochondrial function by administering the compositions to a subject in need thereof.

Although research is ongoing, treatment options for mitochondrial diseases are currently limited; vitamins are frequently prescribed, though the evidence for their effectiveness is limited. Membrane-penetrating antioxidants, pyruvate, and N-acetylcysteine have also been suggested to play a role in improving mitochondrial dysfunction. Further limitations and disadvantages of conventional and traditional approaches will become apparent to one of skill in the art, by comparison of such systems with some aspects of the present invention as set forth in the remainder of the present application with reference to the drawings. There remains an unmet need for potent short- and long-term remedies of mitochondrial diseases.

SUMMARY OF THE INVENTION

The present invention provides cells and methods for treating a variety of mitochondrial diseases. In particular the present invention provides compositions comprising bone-marrow cells which have been enriched with functional mitochondria obtained from healthy donors. The present invention further provides methods for the use of heterologous or autologous "mitochondrially-enriched" bone-marrow cells for treatment of patients. The provision of bone-marrow cells of a patient afflicted with a mitochondrial disease, treated ex-vivo and returned to the same patient, provides great benefits over other methods involving allogeneic cell therapy. For example, the provided methods eliminate the need to screen the population and find a donor which is human leukocyte antigen (HLA)-matched with the patient, which is a lengthy and costly process, and not always successful. The methods further advantageously eliminate the need for life-long immunosuppression therapy of the patient, so that his body does not reject allogeneic cell populations. Thus, the present invention advantageously provides a unique methodology of ex-vivo corrective therapy, in which defective human cells are removed from the patient's body, treated ex-vivo, and returned to the same patient. Moreover, the present invention relates to the administration of bone-marrow cells which, without being bound to any theory or mechanism, are distributed throughout the body in different tissues, and transfer the healthy mitochondria with which they were enriched to the patient's damaged cells.

The present invention is based, in part, on the surprising findings that isolated functional mitochondria can enter intact fibroblasts and bone marrow cells, and that treatment of fibroblasts and bone marrow cells having defective mitochondria with functional mitochondria increases mitochondrial content, cell survival and ATP production.

It has further been surprisingly found that bone-marrow cells are more receptive to be enriched with mitochondria than fibroblast cells, and that human bone-marrow cells are more receptive to be enriched with mitochondria than murine bone-marrow cells. In addition, it has further been surprisingly found that the extent of enrichment of bone-marrow cells with functional mitochondria is dependent in their concentrations or relative proximity, and thus may be manipulated.

More, the present invention is based, in part, on the surprising finding that functional mitochondria, initially comprised in bone-marrow cells, may spontaneously be distributed in-vivo throughout organs, such as the eye, upon injection of the bone-marrow cells directly into the organs. Such findings lay the base for a variety of cellular platforms for delivery of functional mitochondria, and their use in therapy of mitochondrial diseases.

Without being bound to any theory or mechanism, it is hypothesized that co-incubation of bone-marrow cells with isolated functional mitochondria promotes the transition of intact functional mitochondria into the bone-marrow cells. It is further hypothesized that it is the transfer of a corrective component, i.e. a component found in the isolated functional mitochondria that is missing or defective in the mitochondria of bone-marrow cells of patients having a mitochondrial disease, which is responsible for the beneficial effects demonstrated herein for the first time. Without being bound to the above hypotheses, the present invention provides, for the first time, bone-marrow cells of patients of mitochondrial diseases having satisfactory, non-pathologic mitochondrial activity.

Again without being bound to any theory or mechanism, the compositions and methods provided by the present invention may be regarded as a form of "replacement therapy". According to the principles of the present invention, either the mutated genes and/or their missing or un-functional protein products are replaced (or made irrelevant) by wild-type, functional mitochondrial genes and/or functional proteins. Fusion or entry of intact functional mitochondria into bone-marrow cells of mitochondrial disease' patients provides both wild-type mitochondrial genes and functional mitochondrial proteins.

The present invention provides, in one aspect, an ex-vivo method for enriching human bone-marrow cells with functional mitochondria, the method comprising the steps of (i) providing a first composition, comprising a plurality of human bone-marrow cells obtained or derived from a patient afflicted with a mitochondrial disease or from a subject not afflicted with a mitochondrial disease; (ii) providing a second composition, comprising a plurality of isolated human functional mitochondria obtained from a subject not afflicted with a mitochondrial disease; (iii) contacting the human bone-marrow cells of the first composition with the human functional mitochondria of the second composition, thus forming a third composition; and (iv) incubating the third composition under conditions allowing the human functional mitochondria to enter the human bone-marrow cells thereby enriching said human bone-marrow cells with said human functional mitochondria, thus forming a fourth composition; wherein the mitochondrial content of the human bone-marrow cells in the fourth composition is at least 50% higher than the mitochondrial content of the human bone-marrow cells in the first composition.

In certain embodiments, the mitochondrial content of the bone-marrow cells in the first composition or in the fourth composition is determined by determining the content or activity level of citrate synthase. Each possibility represents a separate embodiment of the invention.

In certain embodiments, the bone-marrow cells comprise myelopoietic cells. In certain embodiments, the bone-marrow cells comprise erythropoietic cells. In certain embodiments, the bone-marrow cells comprise multi-potential hematopoietic stem cells (HSCs). In certain embodiments, the bone-marrow cells comprise common myeloid progenitor cells, common lymphoid progenitor cells, or any combination thereof. In certain embodiments, the bone-marrow cells comprise megakaryocytes, erythrocytes, mast cells, myoblasts, basophils, neutrophils, eosinophils, monocytes, macrophages, natural killer (NK) cells, small lymphocytes, T lymphocytes, B lymphocytes, plasma cells, reticular cells, or any combination thereof. In certain embodiments, the bone-marrow cells comprise mesenchymal stem cells. Each possibility represents a separate embodiment of the invention.

In certain embodiments, the bone-marrow cells express the bone-marrow progenitor cell antigen CD34 (CD34$^+$).

In certain embodiments, the bone-marrow cells in the first composition are obtained from the bone marrow of the patient afflicted with a mitochondrial disease, or are obtained from the bone marrow of the subject not afflicted with a mitochondrial disease. In certain embodiments, the bone-marrow cells in the first composition are mobilized from the bone marrow of the patient afflicted with a mitochondrial disease, or are mobilized from the bone marrow of the subject not afflicted with a mitochondrial disease. In certain embodiments, the bone-marrow cells in the first composition are directly obtained from the bone marrow of the patient afflicted with a mitochondrial disease, or are directly obtained from the bone marrow of the subject not afflicted with a mitochondrial disease. In certain embodiments, the bone-marrow cells in the first composition are indirectly obtained from the bone marrow of the patient afflicted with a mitochondrial disease, or are indirectly obtained from the bone marrow of the subject not afflicted with a mitochondrial disease. In certain embodiments, the bone-marrow cells in the first composition are obtained from the peripheral blood of the patient afflicted with a mitochondrial disease, or are obtained from the peripheral blood of the subject not afflicted with a mitochondrial disease. Each possibility represents a separate embodiment of the invention.

In certain embodiments, the method described above further comprises a preceding step, the step comprising administering to the patient afflicted with a mitochondrial disease or to the subject not afflicted with a mitochondrial disease an agent which induces mobilization of bone-marrow cells to peripheral blood. In certain embodiments, the agent is selected from the group consisting of granulocyte-colony stimulating factor (G-CSF), granulocyte-macrophage colony-stimulating factor (GM-CSF), 1,1'-[1,4-Phenylenebis(methylene)]-bis[1,4,8,11-tetraazacyclotetradecane] (Plerixafor), a salt thereof, and any combination thereof. Each possibility represents a separate embodiment of the invention. In certain embodiments, the method described above further comprises a step of isolating the bone-marrow cells from the peripheral blood of the patient afflicted with a mitochondrial disease or from the peripheral blood of the subject not afflicted with a mitochondrial disease. In certain embodiments, the isolation is performed by apheresis.

In certain embodiments, the method described above further comprises concentrating the bone-marrow cells and the functional mitochondria in the third composition before or during incubation. In certain embodiments, the method described above further comprises centrifugation of the third composition before, during or after incubation. Each possibility represents a separate embodiment of the invention.

In certain embodiments, the bone-marrow cells in the first composition are obtained from a patient afflicted with a mitochondrial disease, and have (i) a sub-normal rate of oxygen ($O_2$) consumption; (ii) a sub-normal content or activity level of citrate synthase; (iii) a sub-normal rate of adenosine triphosphate (ATP) production; or (iv) any combination of (i), (ii) and (iii). Each possibility represents a separate embodiment of the invention. In certain embodiments, the heteroplasmy level of the bone-marrow cells in the fourth composition is at least 50% lower than the heteroplasmy level of the bone-marrow cells in the first composition.

In certain embodiments, the bone-marrow cells in the first composition are obtained from a subject not afflicted with a mitochondrial disease, and have (i) a normal rate of oxygen ($O_2$) consumption; (ii) a normal content or activity level of citrate synthase; (iii) a normal rate of adenosine triphosphate (ATP) production; or (iv) any combination of (i), (ii) and (iii). Each possibility represents a separate embodiment of the invention.

In certain embodiments, the isolated human functional mitochondria in the second composition are obtained from a subject not afflicted with a mitochondrial disease, and have (i) a normal rate of oxygen ($O_2$) consumption; (ii) a normal content or activity level of citrate synthase; (iii) a normal rate of adenosine triphosphate (ATP) production; or (iv) any combination of (i), (ii) and (iii). Each possibility represents a separate embodiment of the invention.

In certain embodiments, the bone-marrow cells in the fourth composition have (i) an above-normal rate of oxygen ($O_2$) consumption; (ii) an above-normal content or activity level of citrate synthase; (iii) an above-normal rate of adenosine triphosphate (ATP) production; or (iv) any combination of (i), (ii) and (iii). Each possibility represents a separate embodiment of the invention.

In certain embodiments, the total amount of mitochondrial proteins in the second composition is between 20%-80% of the total amount of cellular proteins within the sample.

In certain embodiments, the fourth composition is not enriched with cytochrome C reductase or cytochrome C reductase activity compared to the first composition.

In certain embodiments, the mitochondrial disease is a mitochondrial respiratory chain disease (MRCD). In certain embodiments, the mitochondrial disease is selected from the group consisting of LHON (Leber's hereditary optic neuropathy); MELAS (mitochondrial myopathy, encephalomyopathy, lactic acidosis, stroke-like symptoms); Pearson syndrome; Leigh syndrome; NARP (neuropathy, ataxia, retinitis pigmentosa, and ptosis); MERRF (myoclonic epilepsy with ragged red fibers); KSS (Kearns-Sayre Syndrome); MNGIE (myoneurogenic gastrointestinal encephalopathy); Friedreich Ataxia; and Alpers' disease. In certain embodiments, the mitochondrial disease is selected from the group consisting of LHON, MELAS, Pearson syndrome, Leigh syndrome, NARP, MERRF, and KSS. Each possibility represents a separate embodiment of the invention. In certain embodiments, the mitochondrial disease is LHON. In certain embodiments, the mitochondrial disease is MELAS.

The present invention further provides, in another aspect, a plurality of human bone-marrow cells enriched with functional mitochondria, obtained by any one of the embodiments of the method described above.

The present invention further provides, in another aspect, a plurality of human bone-marrow cells, wherein the bone-marrow cells (a) have an above-normal mitochondrial content (b) have an above-normal rate of oxygen ($O_2$) consumption; (c) have an above-normal content or activity level of citrate synthase; (d) are CD34$^+$; or (e) any combination thereof. Each possibility represents a separate embodiment of the invention.

In certain embodiments, the plurality of human bone-marrow cells described above is having an above-normal mitochondrial content; having an above-normal rate of oxygen ($O_2$) consumption; having an above-normal content or activity level of citrate synthase; and are $CD34^+$.

The present invention further provides, in another aspect, a pharmaceutical composition comprising a plurality of the human bone-marrow cells described above.

The present invention further provides, in another aspect, the pharmaceutical composition described above for use in a method of treating a mitochondrial disease in a human patient.

The present invention further provides, in another aspect, a method of treating a mitochondrial disease in a human patient in need thereof, comprising the step of administering to the patient the pharmaceutical composition described above.

In certain embodiments, the bone-marrow cells are autologous to the patient afflicted with the mitochondrial disease. In certain embodiments, the bone-marrow cells are exogenous to the patient afflicted with the mitochondrial disease. In certain embodiments, the method described above further comprises a step of administering to the patient an agent which promotes mitochondrial biogenesis. In certain embodiments, the agent which promotes mitochondrial biogenesis is erythropoietin (EPO) or a salt thereof. In certain embodiments, the method described above further comprises a step of administering to the patient an agent which prevents, delays, minimizes or abolishes an adverse immunogenic reaction between the patient and the bone-marrow cells. Each possibility represents a separate embodiment of the invention. In certain embodiments, the adverse immunogenic reaction is a graft-versus-host disease (GvHD). In certain embodiments, the method described above further comprises a step of administering to the patient a pre-transplant conditioning agent prior to the administration of the pharmaceutical composition.

In certain embodiments, the mitochondrial disease is associated with a mutation in the mitochondrial DNA. In certain embodiments, the mitochondrial disease is associated with a mutation in the nuclear DNA. In certain embodiments, the mitochondrial disease is a MRCD. In certain embodiments, the mitochondrial disease is selected from the group consisting of LHON; MELAS; Pearson syndrome; Leigh syndrome; NARP; MERRF; KSS; MNGIE; Friedreich Ataxia; and Alpers' disease. In certain embodiments, the mitochondrial disease is selected from the group consisting of LHON, MELAS, Pearson syndrome, Leigh syndrome, NARP, MERRF, and KSS. Each possibility represents a separate embodiment of the invention. In certain embodiments, the mitochondrial disease is LHON. In certain embodiments, the mitochondrial disease is MELAS.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
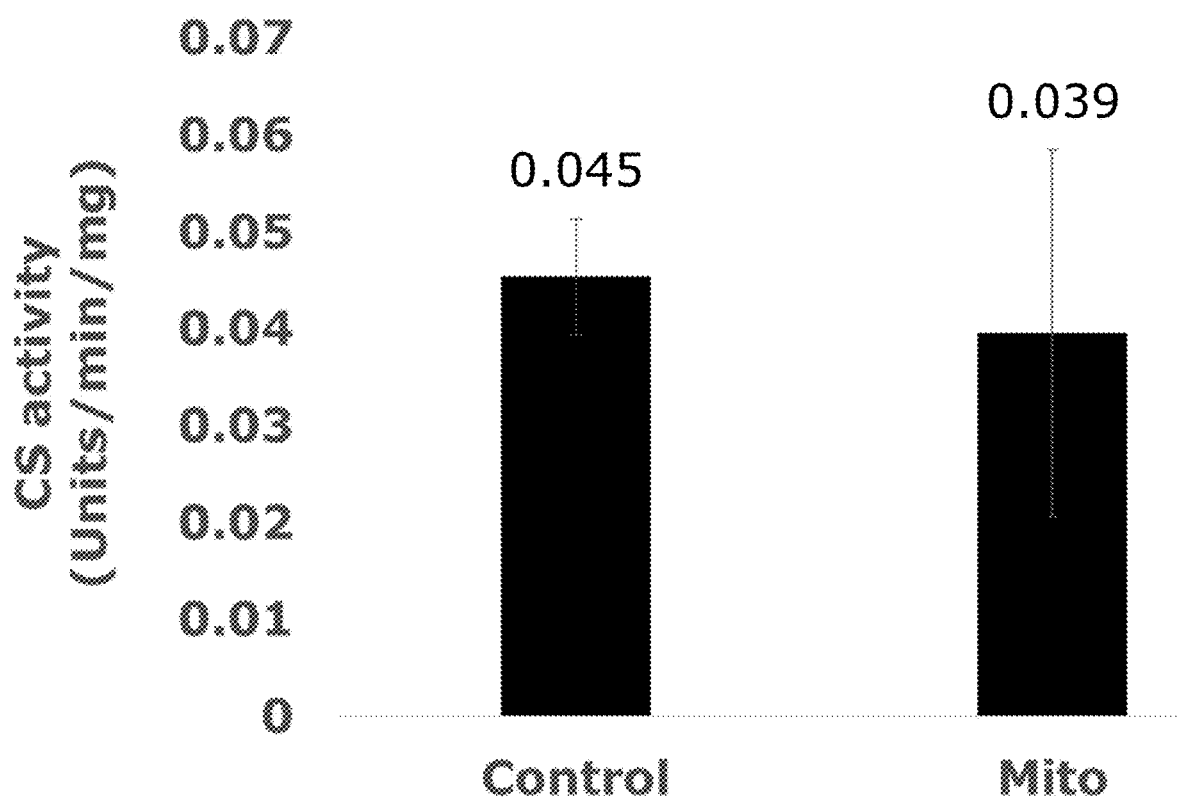
FIG. 1 is a bar graph showing a comparison of citrate synthase (CS) activity in human hepatocyte cells incubated with (Mito) or without (Control) mitochondria isolated from human placental cells.

The present invention provides cellular platforms, more specifically bone-marrow-derived cellular platforms, for targeted and systemic delivery of therapeutically-significant amounts of fully functional, healthy mitochondria. The present invention further provides methods for producing such cellular platforms, and methods for their utilization in treating mitochondrial diseases.

The provision of bone-marrow cells highly enriched with functional mitochondria enables certain therapies of mitochondrial diseases which were not available thus far. For example, mitochondrial diseases associated with mutations (including deletions/insertions) in mitochondrial DNA, such as LHON (Leber's hereditary optic neuropathy) and MELAS (mitochondrial encephalomyopathy, lactic acidosis, and stroke-like episodes) can now be treated by transplanting functional mitochondria into diseased cells, leading to long-term, potentially life-long annulment of the disease. In cases where the affected cells are bone-marrow cells or are derived from bone-marrow cells, the administered bone-marrow cells may also replace the affected cells, again leading to long-term, life-long annulment of the disease. In other examples, where the mitochondrial disease is associated with a mutation (including deletions/insertions) in nuclear DNA and the affected cells are bone-marrow cells or are derived from bone-marrow cells, such as MNGIE and Friedreich's ataxia, the administered bone-marrow cells can replace the affected cells, again leading to long-term, potentially life-long annulment of the disease. It should be emphasized that the present invention provides, for the first time, means and methods for the sustained correction of pathological states of mitochondrial diseases, and therefore annulment of these diseases.

The present invention is based on several surprising findings, amongst which are that (i) the extent of enrichment of bone-marrow cells with intact, functional mitochondria is dependent in their concentrations, and thus may be manipulated, (ii) bone-marrow cells are more receptive to be enriched with mitochondria than fibroblast cells, (iii) human bone-marrow cells are more receptive to be enriched with mitochondria than murine bone-marrow cells, reaching over 8 fold of their natural mitochondrial content, and that (iv) bone marrow cells enriched with normal, functional mitochondria can transfer such mitochondria to the patient's cells.

The present invention provides, in one aspect, an ex-vivo method for enriching human bone-marrow cells with functional mitochondria, the method comprising the steps of (i) providing a first composition, comprising a plurality of human bone-marrow cells obtained or derived from a patient afflicted with a mitochondrial disease or from a subject not afflicted with a mitochondrial disease; (ii) providing a second composition, comprising a plurality of isolated human functional mitochondria obtained from a subject not afflicted with a mitochondrial disease; (iii) contacting the human bone-marrow cells of the first composition with the human functional mitochondria of the second composition, thus forming a third composition; and (iv) incubating the third composition under conditions allowing the human functional mitochondria to enter the human bone-marrow cells thereby enriching said human bone-marrow cells with said human functional mitochondria, thus forming a fourth composition; wherein the mitochondrial content of the human bone-marrow cells in the fourth composition is at least 50% higher than the mitochondrial content of the human bone-marrow cells in the first composition.

The term "ex-vivo method" as used herein refers to any method comprising steps performed exclusively outside the human body.

The term "enriching" as used herein refers to any action designed to increase the mitochondrial content, e.g. the number of intact mitochondria, of a human cell.

The term "human bone-marrow cells" as used herein generally refers to all human cells naturally found in the bone-marrow of humans, and to all cell populations naturally found in the bone-marrow of humans.

The term "functional mitochondria" as used herein refers to mitochondria displaying normal, non-pathologic levels of activity. The activity of mitochondria can be measured by a variety of methods well known in the art, such as $O_2$ consumption, ATP production, and CS activity level.

The phrase "bone-marrow cells obtained from a patient afflicted with a mitochondrial disease or from a subject not afflicted with a mitochondrial disease" as used herein refers to cells that were bone-marrow cells in the patient or subject at the time of their isolation from the patient or subject.

The phrase "bone-marrow cells derived from a patient afflicted with a mitochondrial disease or from a subject not afflicted with a mitochondrial disease" as used herein refers to cells that were not bone-marrow cells in the patient or subject, and have been manipulated to become bone-marrow cells. The term "manipulated" as used herein refers to the use of any one of the methods known in the field (Yu J. et al., Science, 2007, Vol. 318(5858), pages 1917-1920) for reprogramming somatic cells to an undifferentiated state and becoming induced pluripotent stem cells (iPSc), and, optionally, further reprogramming the iPSc to become cells of a desired lineage or population (Chen M. et al., IOVS, 2010, Vol. 51(11), pages 5970-5978), such as bone-marrow cells (Xu Y. et al., 2012, PLoS ONE, Vol. 7(4), page e34321).

The term "a patient afflicted with a mitochondrial disease" as used herein refers to a human subject diagnosed with a mitochondrial disease, suspected to have a mitochondrial disease, or in a risk group of developing a mitochondrial disease. As certain mitochondrial diseases are inherited, the progeny of subjects diagnosed with a mitochondrial disease are considered a risk group of developing a mitochondrial disease.

The term "a subject not afflicted with a mitochondrial disease" as used herein refers to human subject not diagnosed with a mitochondrial disease, not suspected to have a mitochondrial disease, and/or not in a risk group of developing a mitochondrial disease.

The term "induced pluripotent stem cells (iPSc)" as used herein refers to human pluripotent stem cell generated from adult cells.

The term "isolated human functional mitochondria" as used herein refers to intact mitochondria isolated from cells obtained from a subject not afflicted with a mitochondrial disease.

The phrase "conditions allowing the human functional mitochondria to enter the human bone-marrow cells" as used herein generally refers to parameters such as time, temperature, and proximity between the mitochondria and the bone-marrow cells. While identifying those conditions are within the capabilities of any man of ordinary skill in the field, such conditions are provided by the present invention. For example, human cells and human cell lines are routinely incubated in liquid medium, and kept in sterile environments, such as in tissue culture incubators, in 37° C. and 5% $CO_2$ atmosphere.

The term "mitochondrial content" as used herein refers to the amount of functional mitochondria within a cell.

In certain embodiments, the mitochondrial content of the human bone-marrow cells in the fourth composition is at least 100%, 150%, 200%, 250%, 300%, 350%, 400%, 450%, 500%, 550%, 600%, 650%, 700%, 750%, 800%, 850%, 900%, 950%, or 1000% higher than the mitochondrial content of the human bone-marrow cells in the first composition. In certain embodiments, the mitochondrial content of the human bone-marrow cells in the fourth composition is at least 100% higher than the mitochondrial content of the human bone-marrow cells in the first composition. In certain embodiments, the mitochondrial content of the human bone-marrow cells in the fourth composition is at least 200% higher than the mitochondrial content of the human bone-marrow cells in the first composition. In certain embodiments, the mitochondrial content of the human bone-marrow cells in the fourth composition is at least 300% higher than the mitochondrial content of the human bone-marrow cells in the first composition. In certain embodiments, the mitochondrial content of the human bone-marrow cells in the fourth composition is at least 400% higher than the mitochondrial content of the human bone-marrow cells in the first composition. In certain embodiments, the mitochondrial content of the human bone-marrow cells in the fourth composition is at least 500% higher than the mitochondrial content of the human bone-marrow cells in the first composition. In certain embodiments, the mitochondrial content of the human bone-marrow cells in the fourth composition is at least 600% higher than the mitochondrial content of the human bone-marrow cells in the first composition. In certain embodiments, the mitochondrial content of the human bone-marrow cells in the fourth composition is at least 700% higher than the mitochondrial content of the human bone-marrow cells in the first composition. In certain embodiments, the mitochondrial content of the human bone-marrow cells in the fourth composition is at least 750% higher than the mitochondrial content of the human bone-marrow cells in the first composition. In certain embodiments, the mitochondrial content of the human bone-marrow cells in the fourth composition is at least 800% higher than the mitochondrial content of the human bone-marrow cells in the first composition. In certain embodiments, the mitochondrial content of the human bone-marrow cells in the fourth composition is 100%-7900%, 200%-6900%, 300%-5900%, 400%-4900%, 500%-3900%, 600%-2900%, 700%-1900%, or 800%-1400%, higher than the mitochondrial content of the human bone-marrow cells in the first composition. Each possibility represents a separate embodiment of the invention.

In certain embodiments, the first composition is fresh. In certain embodiments, the first composition was frozen and then defrosted. In certain embodiments, the second composition is fresh. In certain embodiments, the second composition was frozen and then defrosted.

Citrate synthase (CS) is localized in the mitochondrial matrix, but is encoded by nuclear DNA. Citrate synthase is involved in the first step of the Krebs cycle, and is commonly used as a quantitative enzyme marker for the presence of intact mitochondria (Larsen S. et al., 2012, J. Physiol., Vol. 590(14), pages 3349-3360; Cook G. A. et al., Biochim. Biophys. Acta., 1983, Vol. 763(4), pages 356-367). In certain embodiments, the mitochondrial content of the bone-marrow cells in the first composition or in the fourth composition is determined by determining the content of citrate synthase. In certain embodiments, the mitochondrial content of the bone-marrow cells in the first composition or in the fourth composition is determined by determining the activity level of citrate synthase. In certain embodiments, the mitochondrial content of the bone-marrow cells in the first composition or in the fourth composition correlates with the content of citrate synthase. In certain embodiments, the mitochondrial content of the bone-marrow cells in the first composition or in the fourth composition correlates with the activity level of citrate synthase.

In certain embodiments, the bone-marrow cells comprise myelopoietic cells. The term "myelopoietic cells" as used herein refers to cells involved in myelopoiesis, e.g. in the production of bone marrow and of all cells that arise from it, namely, all blood cells.

In certain embodiments, the bone-marrow cells comprise erythropoietic cells. The term "erythropoietic cells" as used herein refers to cells involved in erythropoiesis, e.g. in the production of red blood cells (erythrocytes).

In certain embodiments, the bone-marrow cells comprise multi-potential hematopoietic stem cells (HSCs). The term "multi-potential hematopoietic stem cells" or "hemocytoblasts" as used herein refers to the stem cells that give rise to all the other blood cells through the process of haematopoiesis.

In certain embodiments, the bone-marrow cells comprise common myeloid progenitor cells, common lymphoid progenitor cells, or any combination thereof. The term "common myeloid progenitor" as used herein refers to the cells that generate myeloid cells. The term "common lymphoid progenitor" as used herein refers to the cells that generate lymphocytes.

In certain embodiments, the bone-marrow cells comprise megakaryocytes, erythrocytes, mast cells, myoblasts, basophils, neutrophils, eosinophils, monocytes, macrophages, natural killer (NK) cells, small lymphocytes, T lymphocytes, B lymphocytes, plasma cells, reticular cells, or any combination thereof. Each possibility represents a separate embodiment of the invention.

In certain embodiments, the bone-marrow cells comprise mesenchymal stem cells. The term "mesenchymal stem cells" as used herein refers to multipotent stromal cells that can differentiate into a variety of cell types, including osteoblasts (bone cells), chondrocytes (cartilage cells), myocytes (muscle cells) and adipocytes (fat cells).

In certain embodiments, the bone-marrow cells consist of myelopoietic cells. In certain embodiments, the bone-marrow cells consist of erythropoietic cells. In certain embodiments, the bone-marrow cells consist of multi-potential hematopoietic stem cells (HSCs). In certain embodiments, the bone-marrow cells consist of common myeloid progenitor cells, common lymphoid progenitor cells, or any combination thereof. In certain embodiments, the bone-marrow cells consist of megakaryocytes, erythrocytes, mast cells, myoblasts, basophils, neutrophils, eosinophils, monocytes, macrophages, natural killer (NK) cells, small lymphocytes, T lymphocytes, B lymphocytes, plasma cells, reticular cells, or any combination thereof. In certain embodiments, the bone-marrow cells consist of mesenchymal stem cells. Each possibility represents a separate embodiment of the invention.

Hematopoietic progenitor cell antigen CD34 also known as CD34 antigen is a protein that in humans is encoded by the CD34 gene. CD34 is a cluster of differentiation in a cell surface glycoprotein and functions as a cell-cell adhesion factor. In certain embodiments, the bone-marrow cells express the bone-marrow progenitor cell antigen CD34 (are CD34$^+$). In certain embodiments, the bone-marrow cells present the bone-marrow progenitor cell antigen CD34 on their external membrane.

In certain embodiments, the bone-marrow cells in the first composition are directly derived from the patient afflicted with a mitochondrial disease. In certain embodiments, the bone-marrow cells in the first composition are directly derived from the subject not afflicted with a mitochondrial disease. The term "directly derived" as used herein refers to bone-marrow cells which were derived directly from other cells. In certain embodiments, the bone-marrow cells were derived from hematopoietic stem cells (HSc).

In certain embodiments, the bone-marrow cells in the first composition are indirectly derived from the patient afflicted with a mitochondrial disease. In certain embodiments, the bone-marrow cells in the first composition are indirectly derived from the subject not afflicted with a mitochondrial disease. The term "indirectly derived" as used herein refers to bone-marrow cells which were derived from non-bone-marrow cells. In certain embodiments, the bone-marrow cells were derived from somatic cells which were manipulated to become induced pluripotent stem cells (iPSc).

In certain embodiments, the bone-marrow cells in the first composition are directly obtained from the bone marrow of the patient afflicted with a mitochondrial disease. In certain embodiments, the bone-marrow cells in the first composition are directly obtained from the bone marrow of the subject not afflicted with a mitochondrial disease. The term "directly obtained" as used herein refers to bone-marrow cells which were obtained from the bone-marrow itself, e.g. by means such as surgery or suction through a needle by a syringe.

In certain embodiments, the bone-marrow cells in the first composition are indirectly obtained from the bone marrow of the patient afflicted with a mitochondrial disease. In certain embodiments, the bone-marrow cells in the first composition are indirectly obtained from the bone marrow of the subject not afflicted with a mitochondrial disease. The term "indirectly obtained" as used herein refers to bone-marrow cells which were obtained from a location other than the bone-marrow itself.

In certain embodiments, the bone-marrow cells in the first composition are obtained from the peripheral blood of the patient afflicted with a mitochondrial disease. In certain embodiments, the bone-marrow cells in the first composition are obtained from the peripheral blood of the subject not afflicted with a mitochondrial disease. The term "peripheral blood" as used herein refers to blood circulating in the blood system.

In certain embodiments, the method described above further comprises a preceding step, the step comprising administering to the patient afflicted with a mitochondrial disease an agent which induces mobilization of bone-marrow cells to peripheral blood. In certain embodiments, the method described above further comprises a preceding step, the step comprising administering to the subject not afflicted with a mitochondrial disease an agent which induces mobilization of bone-marrow cells to peripheral blood.

In certain embodiments, the agent which induces mobilization of bone-marrow cells to peripheral blood is selected from the group consisting of granulocyte-colony stimulating factor (G-CSF), granulocyte-macrophage colony-stimulating factor (GM-CSF), 1,1'-[1,4-Phenylenebis(methylene)]bis[1,4,8,11-tetraazacyclotetradecane] (Plerixafor, CAS number 155148-31-5), a salt thereof, and any combination thereof. Each possibility represents a separate embodiment of the invention.

In certain embodiments, the method described above further comprises a step of isolating the bone-marrow cells from the peripheral blood of the patient afflicted with a mitochondrial disease. In certain embodiments, the method described above further comprises a step of isolating the bone-marrow cells from the peripheral blood of the subject not afflicted with a mitochondrial disease. The term "isolating from the peripheral blood" as used herein refers to the isolation of bone-marrow cells from other constituents of the blood.

During apheresis, the blood of a donor or patient is passed through an apparatus that separates out one particular constituent and returns the remainder to the circulation. It is thus a medical procedure which is performed outside the body. In certain embodiments, the isolation is performed by apheresis.

In certain embodiments, the method described above further comprises concentrating the bone-marrow cells and the functional mitochondria in the third composition before incubation. In certain embodiments, the method described above further comprises concentrating the bone-marrow cells and the functional mitochondria in the third composition during incubation.

In certain embodiments, the method described above further comprises centrifugation of the third composition before incubation. In certain embodiments, the method described above further comprises centrifugation of the third composition during incubation. In certain embodiments, the method described above further comprises centrifugation of the third composition after incubation.

In certain embodiments, the bone-marrow cells in the first composition are obtained from a patient afflicted with a mitochondrial disease, and the bone-marrow cells have (i) a sub-normal rate of oxygen ($O_2$) consumption; (ii) a sub-normal content or activity level of citrate synthase; (iii) a sub-normal rate of adenosine triphosphate (ATP) production; or (iv) any combination of (i), (ii) and (iii). Each possibility represents a separate embodiment of the invention.

The term "sub-normal rate of oxygen ($O_2$) consumption" as used herein refers to a rate of oxygen ($O_2$) consumption which is substantially lower than a control rate of oxygen ($O_2$) consumption which is derived from or corresponds to the rate of oxygen ($O_2$) consumption found in corresponding cells or corresponding mitochondria of a subject or of a plurality of subjects not afflicted with a mitochondrial disease.

The term "sub-normal content or activity level of citrate synthase" as used herein refers to a content or activity level of citrate synthase which is substantially lower than a control content value or activity level of citrate synthase which is derived from or corresponds to the content or activity level of citrate synthase of a subject or of a plurality of subjects not afflicted with a mitochondrial disease.

The term "sub-normal rate of adenosine triphosphate (ATP) production" as used herein refers to a rate of adenosine triphosphate (ATP) production which is substantially lower than a control rate of adenosine triphosphate (ATP) production which is derived from or corresponds to the rate of adenosine triphosphate (ATP) production found in corresponding cells or corresponding mitochondria of a subject or of a plurality of subjects not afflicted with a mitochondrial disease.

In certain embodiments, the term "substantially lower" as used herein refers to a statistically-significant decrease between the normal and sub-normal values. In certain embodiments, the term "substantially lower" as used herein refers to a pathological decrease, i.e. to a level in which at least one pathological symptom associated with the substantially lower value becomes apparent. In certain embodiments, the term "sub-normal" as used herein refers to a value which is 2 fold, 3 fold, 4 fold, 5 fold, 6 fold, 7 fold, 8 fold, 9 fold, or 10 fold lower than the corresponding value found in corresponding cells or corresponding mitochondria of a subject or of a plurality of subjects not afflicted with a mitochondrial disease. In certain embodiments, the term "sub-normal" as used herein refers to a value which is at least 2 fold, at least 3 fold, at least 4 fold, at least 5 fold, at least 6 fold, at least 7 fold, at least 8 fold, at least 9 fold, or at least 10 fold lower than the corresponding value found in corresponding cells or corresponding mitochondria of a subject or of a plurality of subjects not afflicted with a mitochondrial disease. Each possibility represents a separate embodiment of the invention.

In certain embodiments, the bone-marrow cells in the first composition are obtained from a patient afflicted with a mitochondrial disease, and the bone-marrow cells have (i) a sub-normal rate of oxygen ($O_2$) consumption compared to the rate of oxygen ($O_2$) consumption in bone-marrow cells obtained from a subject or of a plurality of subjects not afflicted with a mitochondrial disease; (ii) a sub-normal content or activity level of citrate synthase compared to the content or activity level of citrate synthase in bone-marrow cells obtained from a subject or of a plurality of subjects not afflicted with a mitochondrial disease; (iii) a sub-normal rate of adenosine triphosphate (ATP) production compared to the rate of adenosine triphosphate (ATP) production in bone-marrow cells obtained from a subject or of a plurality of subjects not afflicted with a mitochondrial disease; or (iv) any combination of (i), (ii) and (iii).

It should be emphasized that any reference to any measurable feature or characteristic or aspect directed to a plurality of cells or mitochondria is directed to the measurable average feature or characteristic or aspect of the plurality of cells or mitochondria.

Heteroplasmy is the presence of more than one type (wild-type/functional vs. mutated/non-functional) of mitochondrial DNA within a cell or individual, and is an important factor in considering the severity of mitochondrial diseases. While low levels of heteroplasmy (sufficient amount of mitochondria are functional) are associated with a healthy phenotype, high levels of heteroplasmy (insufficient amount of mitochondria are functional) are associated with pathologies. In certain embodiments, the heteroplasmy level of the bone-marrow cells in the fourth composition is at least 50% lower than the heteroplasmy level of the bone-marrow cells in the first composition. In certain embodiments, the heteroplasmy level of the bone-marrow cells in the fourth composition is at least 66% lower than the heteroplasmy level of the bone-marrow cells in the first composition. In certain embodiments, the heteroplasmy level of the bone-marrow cells in the fourth composition is at least 75% lower than the heteroplasmy level of the bone-marrow cells in the first composition. In certain embodiments, the heteroplasmy level of the bone-marrow cells in the fourth composition is at least 80% lower than the heteroplasmy level of the bone-marrow cells in the first composition. In certain embodiments, the heteroplasmy level of the bone-marrow cells in the fourth composition is at least 87% lower than the heteroplasmy level of the bone-marrow cells in the first composition. In certain embodiments, the heteroplasmy level of the bone-marrow cells in the fourth composition is at least 90% lower than the heteroplasmy level of the bone-marrow cells in the first composition.

In certain embodiments, the bone-marrow cells in the first composition are obtained from a subject not afflicted with a mitochondrial disease, and have (i) a normal rate of oxygen ($O_2$) consumption; (ii) a normal content or activity level of citrate synthase; (iii) a normal rate of adenosine triphosphate (ATP) production; or (iv) any combination of (i), (ii) and (iii). Each possibility represents a separate embodiment of the invention.

The terms "normal rate of oxygen ($O_2$) consumption" and "control rate of oxygen ($O_2$) consumption" as used herein refer to the rate of oxygen ($O_2$) consumption found in cells or mitochondria of a subject or of a plurality of subjects not afflicted with a mitochondrial disease.

The terms "normal content or activity level of citrate synthase" and "control content or activity level of citrate synthase" as used herein refer to the content or activity level of citrate synthase of a subject or of a plurality of subjects not afflicted with a mitochondrial disease.

The term "normal rate of adenosine triphosphate (ATP) production" and "control rate of adenosine triphosphate (ATP) production" as used herein refer to the rate of adenosine triphosphate (ATP) production found in cells or mitochondria of a subject or of a plurality of subjects not afflicted with a mitochondrial disease.

In certain embodiments, the isolated human functional mitochondria in the second composition are obtained from a subject not afflicted with a mitochondrial disease, and have (i) a normal rate of oxygen ($O_2$) consumption; (ii) a normal content or activity level of citrate synthase; (iii) a normal rate of adenosine triphosphate (ATP) production; or (iv) any combination of (i), (ii) and (iii). Each possibility represents a separate embodiment of the invention.

In certain embodiments, the bone-marrow cells in the fourth composition have (i) an above-normal rate of oxygen ($O_2$) consumption; (ii) an above-normal content or activity level of citrate synthase; (iii) an above-normal rate of adenosine triphosphate (ATP) production; or (iv) any combination of (i), (ii) and (iii). Each possibility represents a separate embodiment of the invention.

The term "above-normal rate of oxygen ($O_2$) consumption" as used herein refers to a rate of oxygen ($O_2$) consumption which is substantially higher than a control rate of oxygen ($O_2$) consumption which is derived from or corresponds to the rate of oxygen ($O_2$) consumption found in corresponding cells or corresponding mitochondria of a subject or of a plurality of subjects not afflicted with a mitochondrial disease.

The term "above-normal content or activity level of citrate synthase" as used herein refers to a content or activity level of citrate synthase which is substantially higher than a control content value or activity level of citrate synthase which is derived from or corresponds to the content or activity level of citrate synthase of a subject or of a plurality of subjects not afflicted with a mitochondrial disease.

The term "above-normal rate of adenosine triphosphate (ATP) production" as used herein refers to a rate of adenosine triphosphate (ATP) production which is substantially higher than a control rate of adenosine triphosphate (ATP) production which is derived from or corresponds to the rate of adenosine triphosphate (ATP) production found in corresponding cells or corresponding mitochondria of a subject or of a plurality of subjects not afflicted with a mitochondrial disease.

In certain embodiments, the term "substantially higher" as used herein refers to a statistically-significant increase between the normal and above-normal values. In certain embodiments, the term "substantially higher" as used herein refers to a non-pathological increase, i.e. to a level in which no pathological symptom associated with the substantially higher value becomes apparent. In certain embodiments, the term "above-normal" as used herein refers to a value which is 2 fold, 3 fold, 4 fold, 5 fold, 6 fold, 7 fold, 8 fold, 8.5 fold, 9 fold, or 10 fold higher than the corresponding value found in corresponding cells or corresponding mitochondria of a subject or of a plurality of subjects not afflicted with a mitochondrial disease. In certain embodiments, the term "above-normal" as used herein refers to a value which is at least 2 fold, at least 3 fold, at least 4 fold, at least 5 fold, at least 6 fold, at least 7 fold, at least 8 fold, at least 8.5 fold, at least 9 fold, or at least 10 fold higher than the corresponding value found in corresponding cells or corresponding mitochondria of a subject or of a plurality of subjects not afflicted with a mitochondrial disease. In certain embodiments, the term "above-normal" as used herein refers to a value which is 2-80 fold, 3-70 fold, 4-60 fold, 5-50 fold, 6-40 fold, 7-30 fold, 8-20 fold, 8.5-20 fold, or 9-15 fold higher than the corresponding value found in corresponding cells or corresponding mitochondria of a subject or of a plurality of subjects not afflicted with a mitochondrial disease. Each possibility represents a separate embodiment of the invention.

In certain embodiments, the bone-marrow cells in the fourth composition have (i) an above-normal rate of oxygen ($O_2$) consumption compared to the rate of oxygen ($O_2$) consumption in bone-marrow cells obtained from a subject or of a plurality of subjects not afflicted with a mitochondrial disease; (ii) an above-normal content or activity level of citrate synthase compared to the content or activity level of citrate synthase in bone-marrow cells obtained from a subject or of a plurality of subjects not afflicted with a mitochondrial disease; (iii) an above-normal rate of adenosine triphosphate (ATP) production compared to the rate of adenosine triphosphate (ATP) production in bone-marrow cells obtained from a subject or of a plurality of subjects not afflicted with a mitochondrial disease; or (iv) any combination of (i), (ii) and (iii). Each possibility represents a separate embodiment of the invention.

In certain embodiments, the total amount of mitochondrial proteins in the second composition is between 20%-80% of the total amount of cellular proteins within the sample.

Eukaroytic NADPH-cytochrome C reductase (cytochrome C reductase) is a flavoprotein localized to the endoplasmic reticulum. It transfers electrons from NADPH to several oxygenases, the most important of which are the cytochrome P450 family of enzymes, responsible for xenobiotic detoxification. Cytochrome C reductase is widely used as an endoplasmic reticulum marker. In certain embodiments, the second composition is substantially free from cytochrome C reductase or cytochrome C reductase activity. In certain embodiments, the fourth composition is not enriched with cytochrome C reductase or cytochrome C reductase activity compared to the first composition.

Mitochondrial Respiratory Chain Disorders (MRCDs) are a heterogeneous group of disorders that share the involvement of the cellular bio-energetic machinery due to molecular defects affecting the mitochondrial oxidative phosphorylation system (OXPHOS). Clinically, they usually involve multiple tissues although they tend to mainly affect nervous system and skeletal muscle. Cardiologic manifestations are frequent and include hypertrophic or dilated cardiomyopathies and heart conduction defects, being part of adult or infantile multi-systemic mitochondrial disorders or, less frequently, presenting as isolated clinical condition. In certain embodiments, the mitochondrial disease is a mitochondrial respiratory chain disease (MRCD).

In certain embodiments, the mitochondrial disease is selected from the group consisting of LHON (Leber's hereditary optic neuropathy); MELAS (mitochondrial myopathy, encephalomyopathy, lactic acidosis, stroke-like symptoms); Pearson syndrome; Leigh syndrome; NARP (neuropathy, ataxia, retinitis pigmentosa, and ptosis); MERRF (myoclonic epilepsy with ragged red fibers); KSS (Kearns-Sayre Syndrome); MNGIE (myoneurogenic gastro-intestinal encephalopathy); Friedreich Ataxia; and Alpers' disease. In certain embodiments, the mitochondrial disease is selected from the group consisting of LHON, MELAS, Pearson syndrome, Leigh syndrome, NARP, MERRF, and KSS. Each possibility represents a separate embodiment of the invention. In certain embodiments, the mitochondrial disease is LHON. In certain embodiments, the mitochondrial disease is MELAS.

In certain embodiments, the method further comprises freezing the fourth composition. In certain embodiments, the method further comprises freezing and then defrosting the fourth composition.

The present invention further provides, in another aspect, a plurality of human bone-marrow cells enriched with functional mitochondria, obtained by the method described above.

In certain embodiments, the plurality is frozen. In certain embodiments, the plurality is frozen and then defrosted.

The present invention further provides, in another aspect, a plurality of human bone-marrow cells, wherein the bone-marrow cells (a) have an above-normal mitochondrial content (b) have an above-normal rate of oxygen ($O_2$) consumption; (c) have an above-normal content or activity level of citrate synthase; (d) are $CD34^+$; or (v) any combination of (a), (b), (c) and (d). Each possibility represents a separate embodiment of the invention.

The term "above-normal mitochondrial content" as used herein refers to a mitochondrial content which is substantially higher than a control mitochondrial content which is derived from or corresponds to the mitochondrial content found in corresponding cells of a subject or of a plurality of subjects not afflicted with a mitochondrial disease.

In certain embodiments, the plurality is frozen. In certain embodiments, the plurality is frozen and then defrosted.

In certain embodiments, the plurality of human bone-marrow cells described above is having an above-normal mitochondrial content; having an above-normal rate of oxygen ($O_2$) consumption; having an above-normal content or activity level of citrate synthase; and are $CD34^+$.

The present invention further provides, in another aspect, a pharmaceutical composition comprising a plurality of human bone-marrow cells as described above.

The term "pharmaceutical composition" as used herein refers to any composition comprising at least one biologically active agent.

The term "biologically active agent" as used herein refers to any molecule capable of eliciting a response in a biological system such as, for example, living cell(s), tissue(s), organ(s), and being(s). Non-limiting examples of biologically active agents according to the present inventions include cells, intact mitochondria, mitochondrial DNA, and a mitochondrial protein.

In certain embodiments, the pharmaceutical composition is frozen. In certain embodiments, the pharmaceutical composition is frozen and then defrosted.

In certain embodiments, the pharmaceutical composition described above is for use in a method of treating a mitochondrial disease in a human patient. The term "treating" as used herein includes the diminishment, alleviation, or amelioration of at least one symptom associated or induced by a disease or condition. The term "treating" as used herein also includes preventative (e.g., prophylactic), palliative and curative treatment.

The present invention further provides, in another aspect, a method of treating a mitochondrial disease in a human patient in need thereof, comprising the step of administering to the patient the pharmaceutical composition described above.

The term "method" as used herein generally refers to manners, means, techniques and procedures for accomplishing a given task, including, but not limited to, those manners, means, techniques and procedures either known to, or readily developed from known manners, means, techniques and procedures by practitioners of the chemical, pharmacological, biological, biochemical and medical arts.

In certain embodiments, the pharmaceutical composition is frozen, and the method described above further comprises defrosting the frozen pharmaceutical composition.

In certain embodiments, the bone-marrow cells are autologous to the patient afflicted with the mitochondrial disease. The term "autologous to the patient" as used herein refers to the bone-marrow cells and other cells of the patient being HLA-matched.

In certain embodiments, the bone-marrow cells are exogenous to the patient afflicted with the mitochondrial disease. The term "exogenous to the patient" as used herein refers to the bone-marrow cells and other cells of the patient not being HLA-matched.

In certain embodiments, the method described above further comprises a step of administering to the patient an agent which promotes mitochondrial biogenesis. The term "mitochondrial biogenesis" as used herein refers to the growth and division of mitochondria. In certain embodiments, the agent which promotes mitochondrial biogenesis is erythropoietin (EPO) or a salt thereof. In certain embodiments, the agent is selected from the group consisting of recombinant human erythropoietin and isolated human erythropoietin.

In certain embodiments, the method described above further comprises a step of administering to the patient an agent which prevents, delays, minimizes or abolishes an adverse immunogenic reaction between the patient and the bone-marrow cells. In certain embodiments, the adverse immunogenic reaction is a graft-versus-host disease (GvHD). In certain embodiments, the GvHD is an acute form of the disease (aGvHD). In certain embodiments, the GvHD is a chronic form of the disease (cGvHD).

In certain embodiments, the method described above further comprises a preceding step of administering to the patient a pre-transplant conditioning agent prior to the administration of the pharmaceutical composition. The term "pre-transplant conditioning agent" as used herein refers to any agent capable of killing bone-marrow cells within the bone-marrow of a human subject. In certain embodiments, the pre-transplant conditioning agent is Busulfan.

In certain embodiments, the mitochondrial disease is associated with a mutation in the mitochondrial DNA. In certain embodiments, the mitochondrial disease is associated with a mutation in the nuclear DNA. The term "mutation" as used herein refers to an insertion, deletion or replacement of at least one nucleotide in mitochondrial or nuclear DNA.

In certain embodiments, the mitochondrial disease is a MRCD. In certain embodiments, the mitochondrial disease is selected from the group consisting of LHON; MELAS; Pearson syndrome; Leigh syndrome; NARP; MERRF; KSS; MNGIE; Friedreich Ataxia; and Alpers' disease. In certain embodiments, the mitochondrial disease is selected from the group consisting of LHON, MELAS, Pearson syndrome, Leigh syndrome, NARP, MERRF, and KSS. In certain embodiments, the mitochondrial disease is LHON. In certain embodiments, the mitochondrial disease is MELAS.

In certain embodiments, the pharmaceutical composition is administered locally. In certain embodiments, the administration of the pharmaceutical composition to a subject is by direct administration to the bone-marrow of the subject. In certain embodiments, the administration of the pharmaceutical composition to a subject is to a tissue or an organ. In certain embodiments, the administration of the pharmaceutical composition to a subject is to the eye. The vitreous humour is a transparent, colorless, gelatinous mass that fills the space in the eye between the lens and the retina. In certain embodiments, the administration of the pharmaceutical composition to a subject is to the vitreous humour of the eye. In certain embodiments, the administration of the pharmaceutical composition to a subject is by direct intramuscular injection. In certain embodiments, the pharmaceutical composition is administered systemically. In certain embodiments, the administration of the pharmaceutical composition to a subject is by a route selected from the group consisting of intravenous, intraarterial, intramuscular, subcutaneous, and direct injection into a tissue or an organ. Each possibility represents a separate embodiment of the invention.

In certain embodiments, the functional mitochondria are obtained from a human cell or a human tissue selected from the group consisting of placenta, placental cells grown in culture, and blood cells. Each possibility represents a separate embodiment of the invention.

According to certain embodiments, the functional mitochondria have undergone a freeze-thaw cycle. Without wishing to be bound by any theory or mechanism, mitochondria that have undergone a freeze-thaw cycle demonstrate a comparable oxygen consumption rate following thawing, as compared to control mitochondria that have not undergone a freeze-thaw cycle.

According to some embodiments, the freeze-thaw cycle comprises freezing said functional mitochondria for at least 24 hours prior to thawing. According to some embodiments, the freeze-thaw cycle comprises freezing said functional mitochondria for at least 1 month prior to thawing, several months prior to thawing or longer. According to another embodiment, the oxygen consumption of the functional mitochondria after the freeze-thaw cycle is equal or higher than the oxygen consumption of the functional mitochondria prior to the freeze-thaw cycle.

As used herein, the term "freeze-thaw cycle" refers to freezing of the functional mitochondria to a temperature below 0° C., maintaining the mitochondria in a temperature below 0° C. for a defined period of time and thawing the mitochondria to room temperature or body temperature or any temperature above 0° C. which enables treatment of the hematopoietic cells with the mitochondria. Each possibility represents a separate embodiment of the present invention. The term "room temperature", as used herein refers to a temperature of between 18° C. and 25° C. The term "body temperature", as used herein, refers to a temperature of between 35.5° C. and 37.5° C., preferably 37° C. In another embodiment, mitochondria that have undergone a freeze-thaw cycle are functional mitochondria.

In another embodiment, the mitochondria that have undergone a freeze-thaw cycle were frozen at a temperature of −70° C. or lower. In another embodiment, the mitochondria that have undergone a freeze-thaw cycle were frozen at a temperature of −20° C. or lower. In another embodiment, the mitochondria that have undergone a freeze-thaw cycle were frozen at a temperature of −4° C. or lower. In another embodiment, the mitochondria that have undergone a freeze-thaw cycle were frozen at a temperature of 0° C. or lower. According to another embodiment, freezing of the mitochondria is gradual. According to some embodiment, freezing of mitochondria is through flash-freezing. As used herein, the term "flash-freezing" refers to rapidly freezing the mitochondria by subjecting them to cryogenic temperatures.

In another embodiment, the mitochondria that underwent a freeze-thaw cycle were frozen for at least 30 minutes prior to thawing. According to another embodiment, the freeze-thaw cycle comprises freezing the functional mitochondria for at least 30, 60, 90, 120, 180, 210 minutes prior to thawing. Each possibility represents a separate embodiment of the present invention. In another embodiment, the mitochondria that have undergone a freeze-thaw cycle were frozen for at least 1, 2, 3, 4, 5, 6, 7, 8, 9, 10, 24, 48, 72, 96, or 120 hours prior to thawing. Each freezing time presents a separate embodiment of the present invention. In another embodiment, the mitochondria that have undergone a freeze-thaw cycle were frozen for at least 4, 5, 6, 7, 30, 60, 120, 365 days prior to thawing. Each freezing time presents a separate embodiment of the present invention. According to another embodiment, the freeze-thaw cycle comprises freezing the functional mitochondria for at least 1, 2, 3 weeks prior to thawing. Each possibility represents a separate embodiment of the present invention. According to another embodiment, the freeze-thaw cycle comprises freezing the functional mitochondria for at least 1, 2, 3, 4, 5, 6 months prior to thawing. Each possibility represents a separate embodiment of the present invention.

In another embodiment, the mitochondria that have undergone a freeze-thaw cycle were frozen at −70° C. for at least 30 minutes prior to thawing. Without wishing to be bound by any theory or mechanism, the possibility to freeze mitochondria and thaw them after a long period enables easy storage and use of the mitochondria with reproducible results even after a long period of storage.

According to another embodiment, thawing is at room temperature. In another embodiment, thawing is at body temperature. According to another embodiment, thawing is at a temperature which enables administering the mitochondria according to the methods of the invention. According to another embodiment, thawing is performed gradually.

According to another embodiment, the mitochondria that underwent a freeze-thaw cycle were frozen within a freezing buffer. According to another embodiment, the mitochondria that underwent a freeze-thaw cycle were frozen within the isolation buffer. As used herein, the term "isolation buffer" refers to a buffer in which the mitochondria of the invention have been isolated. In a non-limiting example, the isolation buffer is a sucrose buffer. Without wishing to be bound by any mechanism or theory, freezing mitochondria within the isolation buffer saves time and isolation steps, as there is no need to replace the isolation buffer with a freezing buffer prior to freezing or to replace the freezing buffer upon thawing.

According to another embodiment, the freezing buffer comprises a cryoprotectant. According to some embodiments, the cryoprotectant is a saccharide, an oligosaccharide or a polysaccharide. Each possibility represents a separate embodiment of the present invention. According to another embodiment, the saccharide concentration in the freezing buffer is a sufficient saccharide concentration which acts to preserve mitochondrial function. According to another embodiment, the isolation buffer comprises a saccharide. According to another embodiment, the saccharide concentration in the isolation buffer is a sufficient saccharide concentration which acts to preserve mitochondrial function. According to another embodiment, the saccharide is sucrose.

According to another embodiment, the intactness of a mitochondrial membrane may be determined by any method known in the art. In a non-limiting example, intactness of a mitochondrial membrane is measured using the tetramethylrhodamine methyl ester (TMRM) or the tetramethylrhodamine ethyl ester (TMRE) fluorescent probes. Each possibility represents a separate embodiment of the present invention. Mitochondria that were observed under a microscope and show TMRM or TMRE staining have an intact mitochondrial outer membrane. As used herein, the term "a mitochondrial membrane" refers to a mitochondrial membrane selected from the group consisting of the mitochondrial inner membrane, the mitochondrial outer membrane, and both.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1. Isolated Mitochondria Cannot Enter Human Hepatocyte Cells

Human HepG2 cells ($10^5$, ATCC HB-8065) were untreated (control) or incubated for 24 hours with mitochondria isolated from human placental cells. Before plating the cells, mitochondria were mixed with the cells, centrifuged at 8000 g and re-suspended. After incubation, the cells were washed twice with PBS, and CS activity was measured using the CS0720 Sigma kit (FIG. 1).

The results demonstrated in FIG. 1 indicate that mitochondria cannot enter human hepatocyte cells, even after co-centrifugation.

Example 2. Isolated Mitochondria can Enter Fibroblast Cells

Mouse fibroblast cells (3T3) expressing green fluorescent protein (GFP) in their mitochondria (left panel) were incubated for 24 hours with red fluorescent protein (RFP)-labeled mitochondria isolated from mouse fibroblasts (3T3) expressing RFP in their mitochondria (middle panel). Fluorescent confocal microscopy was used to identify fibroblasts labeled with both GFP and RFP, which appear yellow (right panel) (FIG. 2).

Figure 2:
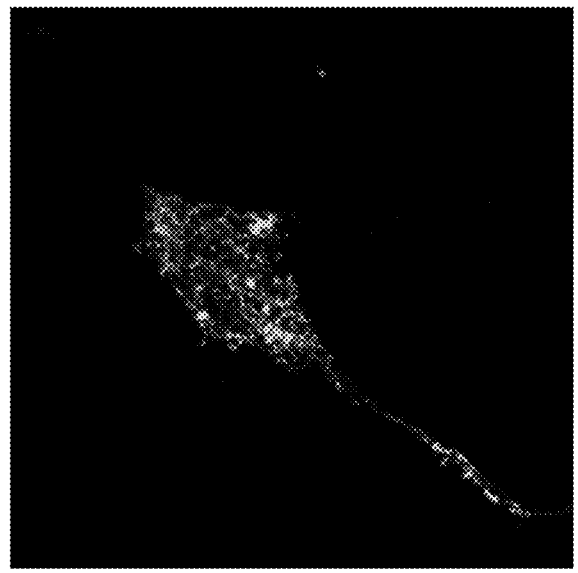
FIG. 2 is three micrographs showing mouse fibroblast cell expressing mitochondrial GFP (left panel), incubation with isolated RFP-labeled mitochondria (middle panel), and an overlay (right panel), obtained by fluorescence confocal microscopy.
Figure 2:
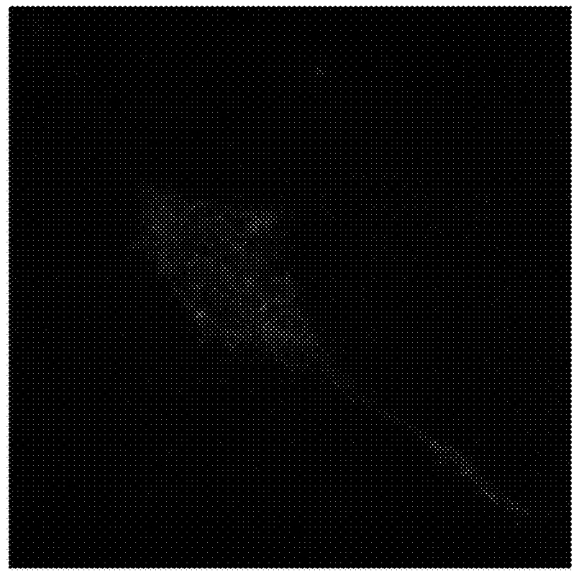
Figure 2:
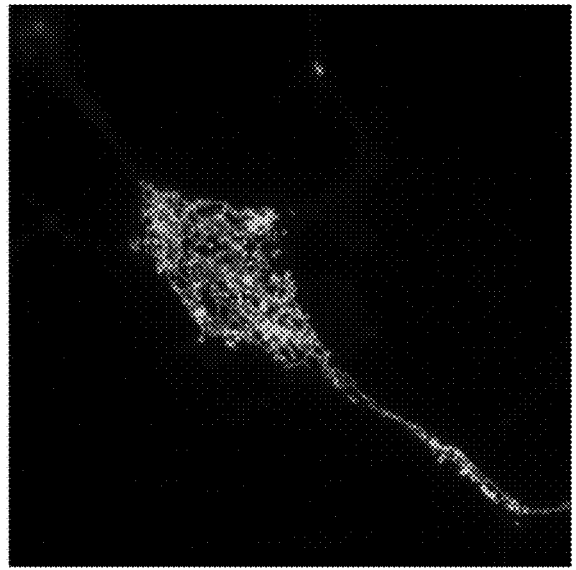

The results demonstrated in FIG. 2 indicate that mitochondria can enter fibroblast cells.

Figure 3:
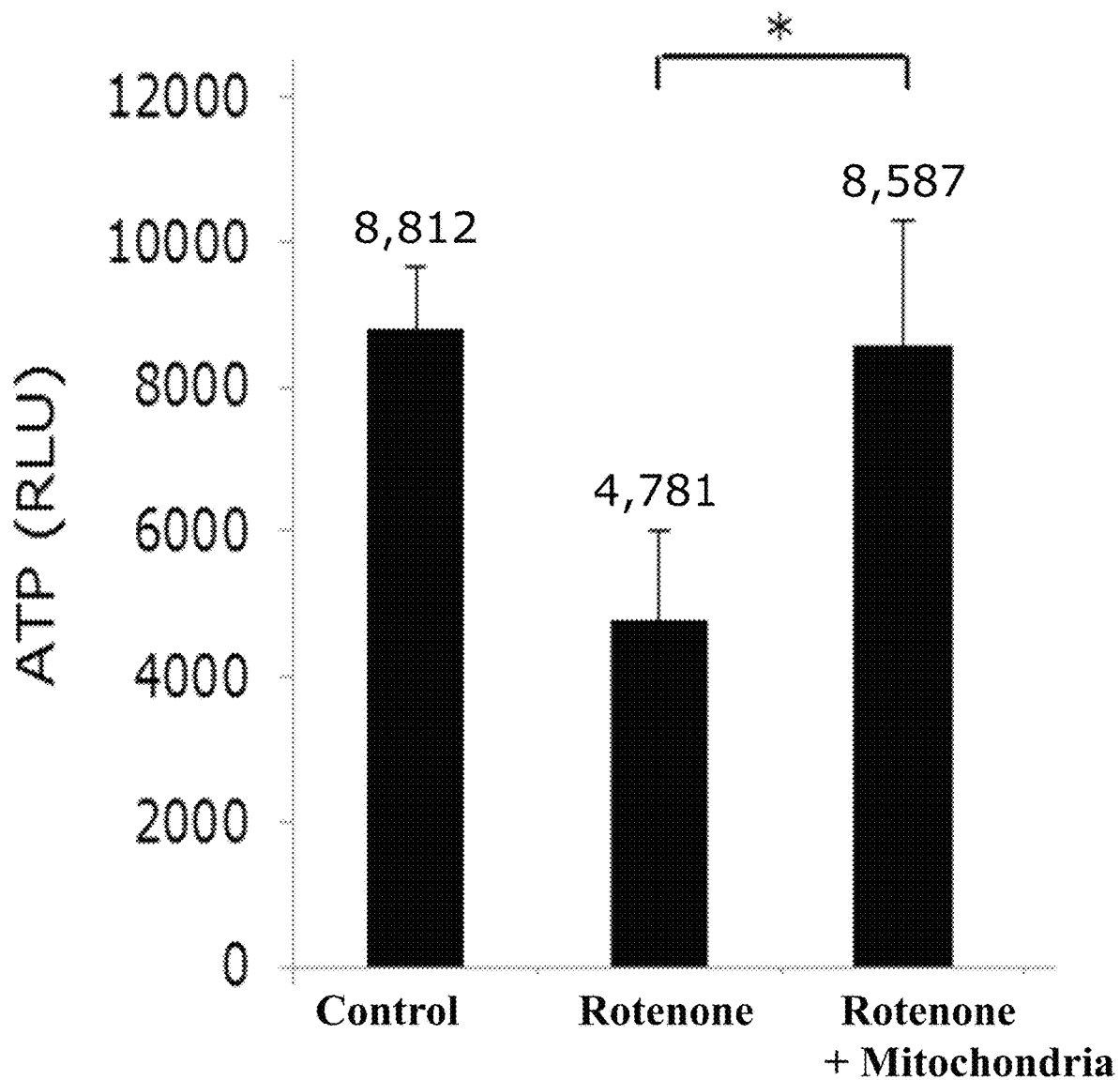
FIG. 3 is a bar graph showing a comparison of ATP levels in mouse fibroblast cells which were either untreated (Control), treated with a mitochondrial complex I irreversible inhibitor (Rotenone), or treated with Rotenone and mouse placental mitochondria (Rotenone+Mitochondria). Data is presented as mean values±SEM, (*) p value<0.05. RLU—relative luminescence units.

Example 3. Mitochondria Increase ATP Production in Cells with Inhibited Mitochondrial Activity Mouse fibroblast cells ($10^4$, 3T3) were either not treated (control) or treated with 0.5 µM Rotenone (Rotenone, mitochondrial complex I irreversible inhibitor, CAS number 83-79-4) for 4 hours, washed, and further treated with 0.02 mg/ml mouse placental mitochondria (Rotenone+Mitochondria) for 3 hours. The cells were washed and ATP level was determined using the Perkin Elmer ATPlite kit (FIG. 3). As seen in FIG. 3, the production of ATP was completely rescued in cells incubated with mitochondria compared to control.

The results demonstrated in FIG. 3 clearly indicate that while Rotenone alone decreased ATP levels by about 50%, the addition of mitochondria was capable of substantially cancelling the inhibitory effect of Rotenone, reaching the ATP levels of the control cells. The experiment provides evidence to the capability of mitochondria to increase mitochondrial ATP production in cells of abrogated mitochondrial activity.

Example 4. Mitochondria can Enter Murine Bone Marrow Cells

Mouse bone-marrow cells ($10^5$) were incubated for 24 hours with GFP-labeled mitochondria, isolated from mouse melanoma cells. Fluorescence confocal microscopy was used to identify GFP-labeled mitochondria inside the bone marrow cells (FIG. 4).

Figure 4:
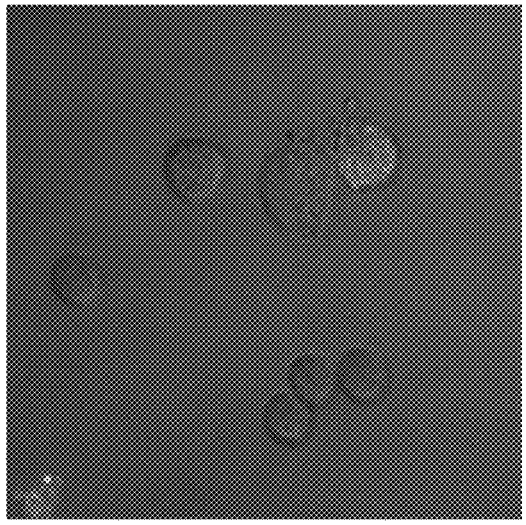
FIG. 4 is four micrographs obtained by fluorescence confocal microscopy showing mouse bone marrow cells incubated with GFP-labeled mitochondria isolated from mouse melanoma cells.
Figure 4:
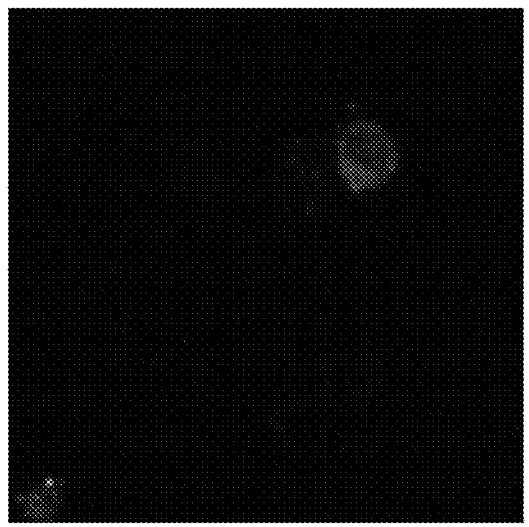
Figure 4:
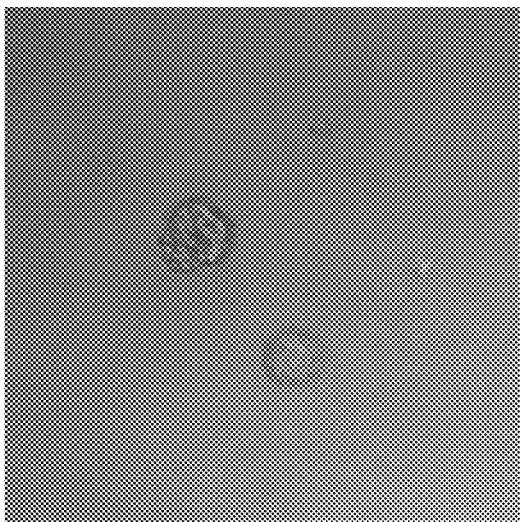
Figure 4:
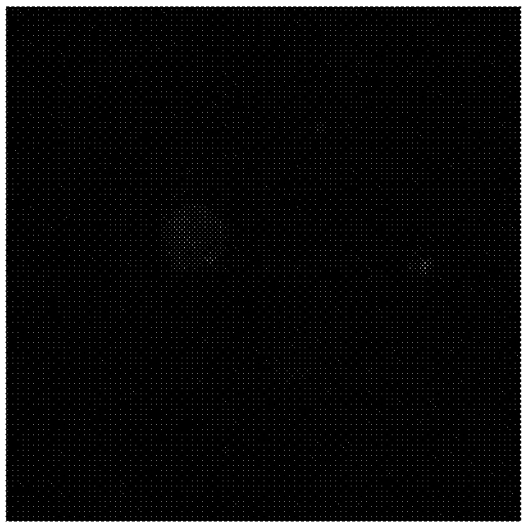

The results demonstrated in FIG. 4 indicate that mitochondria can enter bone marrow cells.

Figure 5:
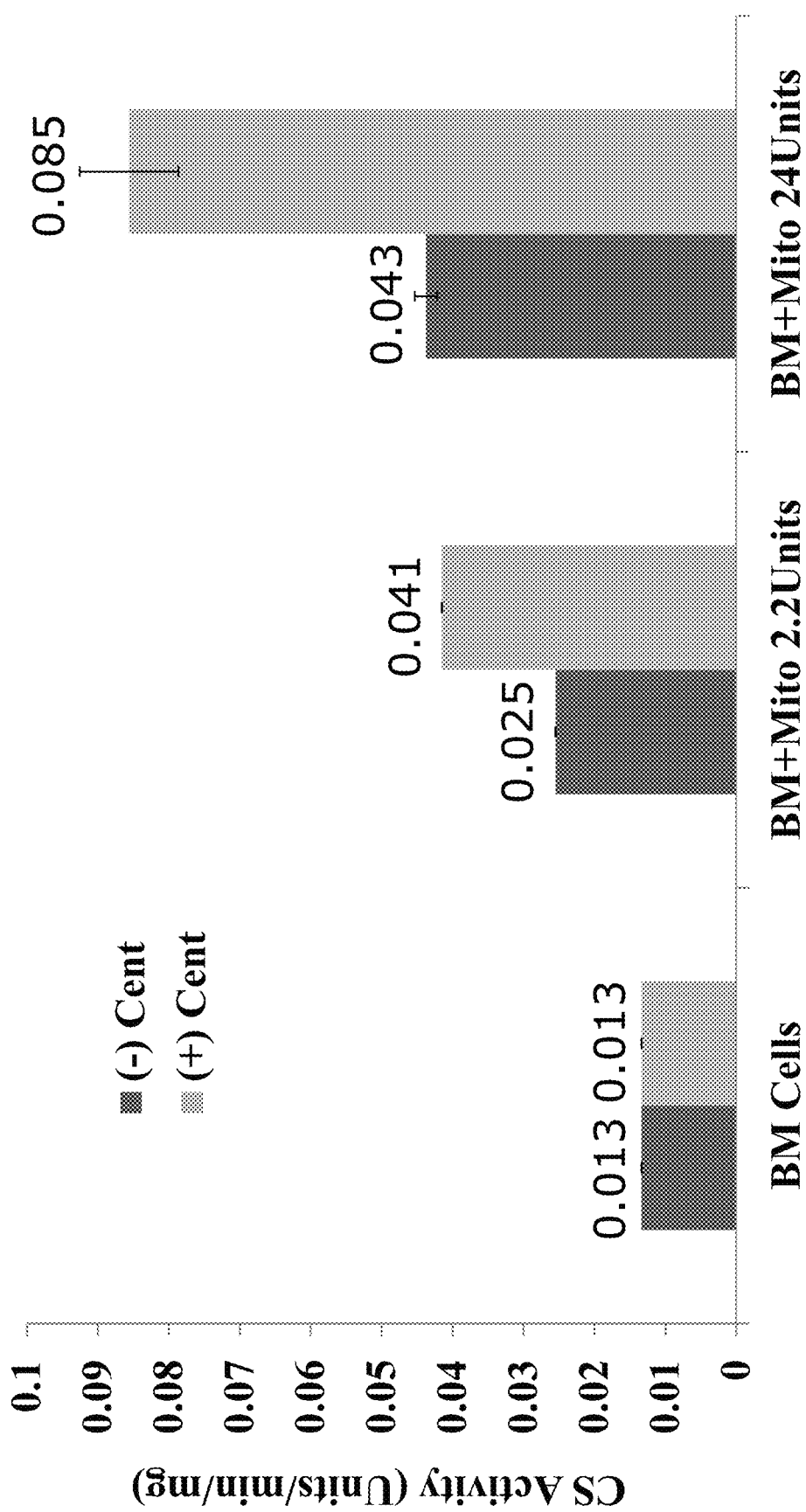
FIG. 5 is a bar graph showing a comparison of citrate synthase (CS) activity in mouse bone marrow (BM) cells incubated with varying amounts of GFP-labeled mitochondria isolated from mouse melanoma cells, with or without centrifugation.

Example 5. Mitochondria Enter Bone Marrow Cells in a Concentration-Dependent Manner Mouse bone marrow cells ($10^6$) were untreated or incubated for 15 hours with different amounts of GFP-labeled mitochondria isolated from mouse melanoma cells. Before plating the cells, mitochondria were mixed with the cells and either left to stand for 5 minutes at room temperature ((−) Cent) or centrifuged for 5 minutes at 8,000 g at 4° C. ((+) Cent). The cells were then plated in 24 wells ($10^6$ cells/well). After 15 hours of incubation, the cells were washed twice to remove any mitochondria that did not enter the cells. Citrate synthase activity was determined using the CS0720 Sigma kit (FIG. 5). The CS activity levels measured under the conditions specified above are summarized in Table 1.

TABLE 1

|  | (+) Cent | (−) Cent | (+) Cent, normalized | (−)Cent, normalized |
|---|---|---|---|---|
| Cells | 0.013368 | 0.013368 | 1 | 1 |
| Cells + Mitochondria (2.2 units) | 0.041512 | 0.025473 | 3.1 | 1.9 |
| Cells + Mitochondria (24 units) | 0.085606 | 0.04373 | 6.4 | 3.2 |

The results demonstrated in FIG. 5 indicate that added mitochondria increase cellular CS activity in a dose-dependent manner, and that increasing the concentration and therefore presumingly the contact between the mitochondria and cells, e.g. by centrifugation, resulted in a further increase in CS activity.

Example 6. Specific Mitochondrial Enrichment with No ER Contamination

Figure 6A:
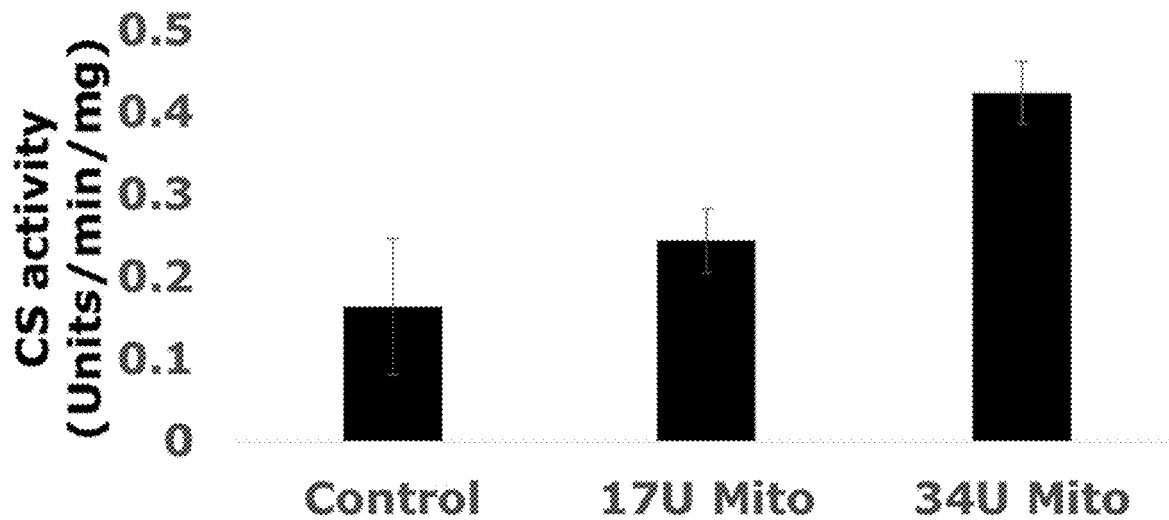
FIG. 6A is a bar graph showing a comparison of CS activity in murine BM cells after enrichment with increasing amounts of GFP-labeled mitochondria.
Figure 6B:
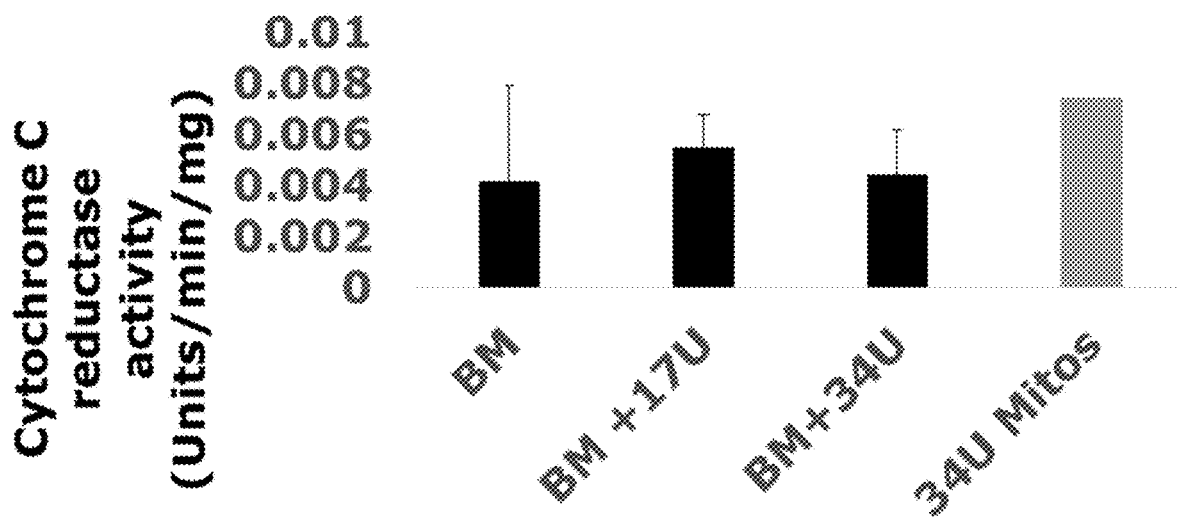
FIG. 6B is a bar graph showing a comparison of cytochrome c reductase activity in these cells (black bars), compared to the activity in GFP-labeled mitochondria (gray bar).

Mouse bone-marrow cells ($10^6$) were untreated or incubated for 24 hours with GFP-labeled mitochondria isolated from mouse melanoma cells (17U or 34U, indicating the level of citrate synthase activity as a marker for mitochondria content). The cells were mixed with mitochondria, centrifuged at 8000 g and re-suspended. After 24 hour incubation, the cells were washed twice with PBS and the level of citrate synthase (CS) activity (FIG. 6A) and cytochrome c reductase activity (FIG. 6B) were measured using the CS0720 and CY0100 kits (Sigma), respectively.

The results demonstrated in FIG. 6 clearly indicate that the compositions of functional mitochondria used in the experiments above enrich bone-marrow cells with mitochondria, but not with ER.

Figure 7A:
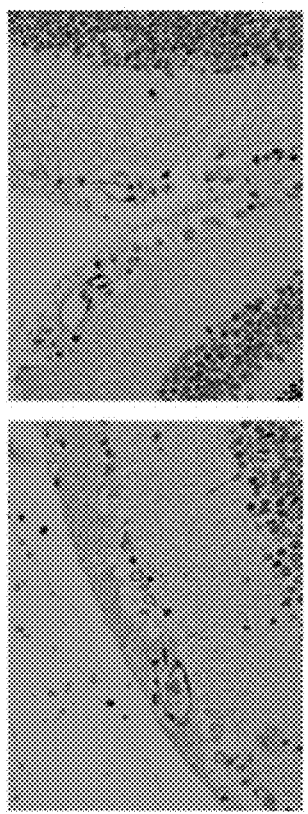
FIG. 7A depict the results of GFP staining in control, untreated murine eyeballs.
Figure 7B:
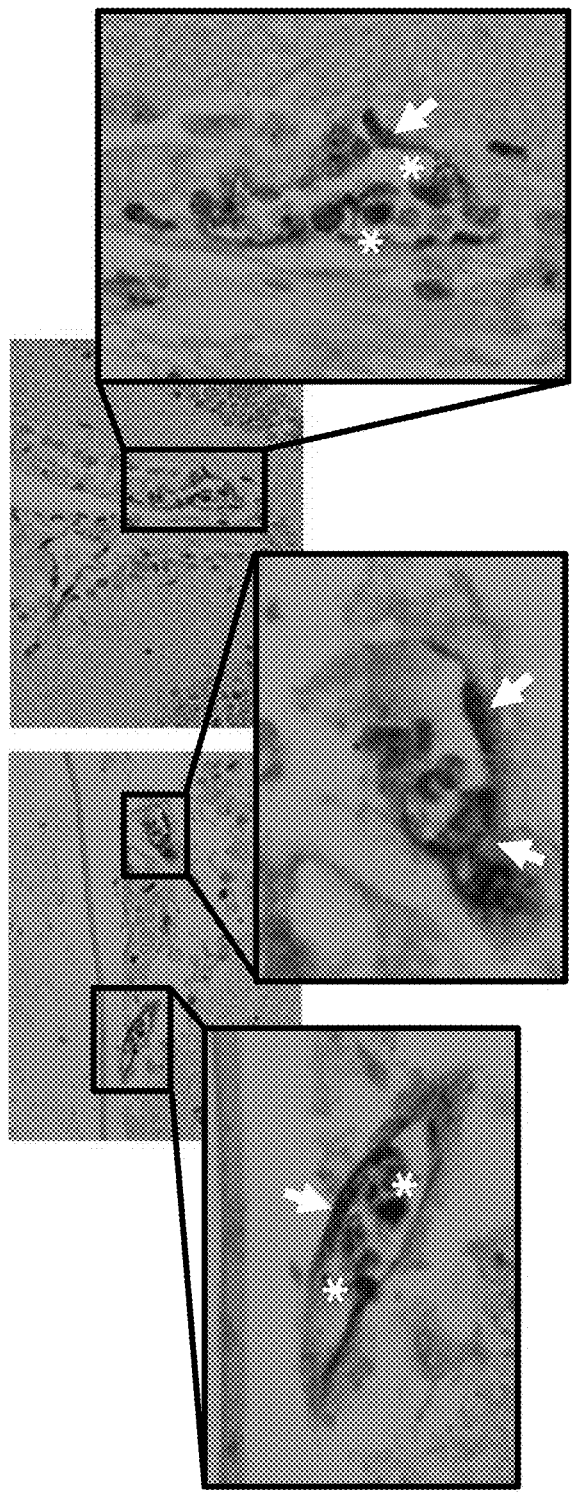
FIG. 7B depict the results of GFP staining in murine eyeballs injected with murine BM cells incubated with GFP-labeled mitochondria after centrifugation. (*) GFP-labeled cells inside blood vessels in the retinal ganglion cells layer. (→) cells lining the wall of blood vessels.

Example 7. Murine Bone Marrow Cells Enriched with Mitochondria Distribute Mitochondria in an In-Vivo Model of LHON Mouse bone-marrow cells ($10^5$) were untreated or incubated for 24 hours with GFP-labeled mitochondria isolated from mouse melanoma cells. The cells were mixed with mitochondria, centrifuged at 8000 g and re-suspended. After 24 hour incubation, the cells were washed twice with PBS and injected intra-vitrealy 4 hours after rotenone injection (25 mM). Paraffin sections were stained using Immunohistochemistry with anti-GFP antibody. FIG. 7A depicts the staining of slices of Control 1 (no cells or mitochondria injected, left panel) and Control 2 (cells loaded with mitochondria injected, but no anti-GFP used in staining, right panel). FIG. 7B depicts the staining of slices of an injected eyeball. GFP-positive cells were observed in the Retinal Ganglion Cell (RGC) layer (two upper panels), in blood vessels (*) and in cells lining the wall of blood vessels (arrow).

The results demonstrated in FIG. 7 clearly indicate that bone-marrow cells can act as carriers for mitochondria and are able to distribute functional mitochondria in target organs or tissues. This capability can further be utilized to treat various other mitochondrial diseases.

Example 8. Mitochondria Increase Proliferation of Human mtDNA-Depleted Cells

Figure 8A:
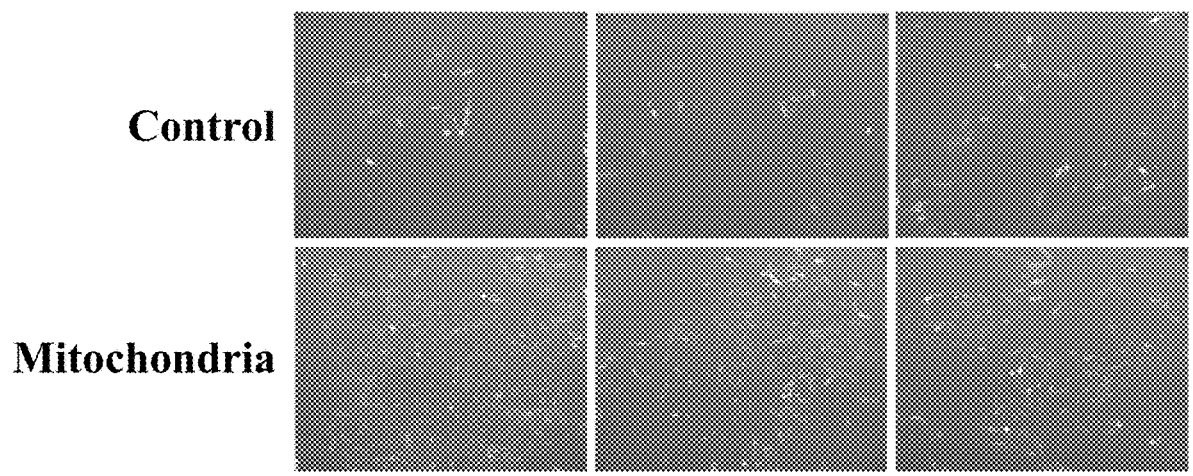
FIG. 8A depicts the increase in viability of mitochondrial DNA- (mtDNA-) deficient human 143B osteosarcoma cells (Control, upper three panels) by mitochondria isolated from mtDNA-containing cells (Mitochondria, lower three panels).
Figure 8B:
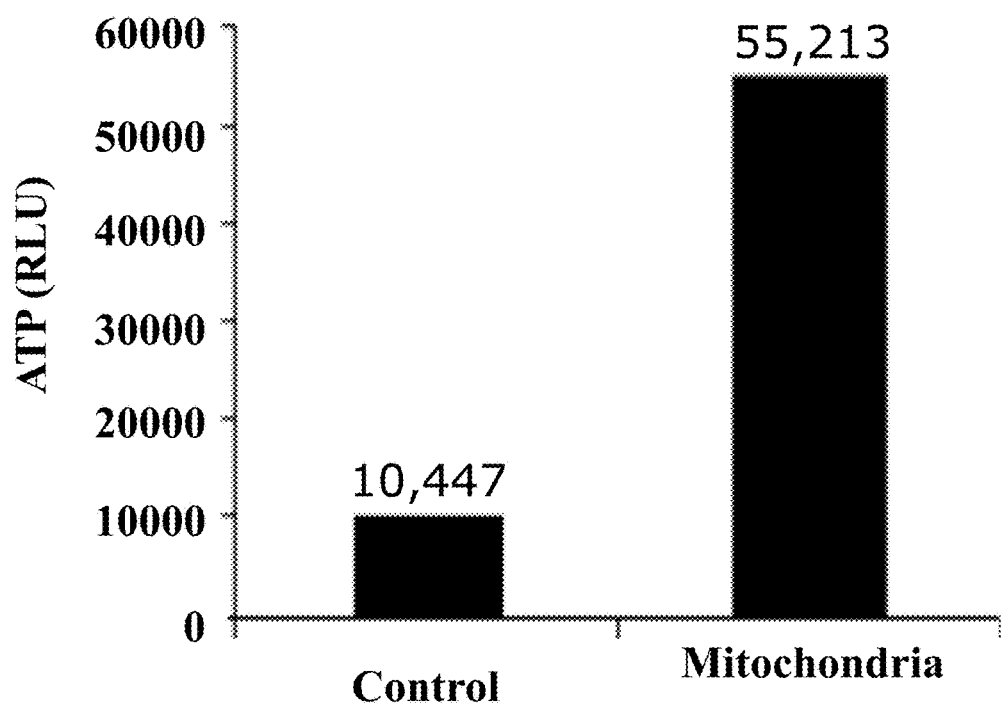
FIG. 8B is a bar graph showing a comparison of ATP levels in the cells presented in FIG. 8A.

143B Rho0 cells (human bone osteosarcoma, mitochondrial-DNA deficient (mtDNA$^-$) were seeded in 96 wells ($3*10^4$ cells/well) and cultured in medium containing pyruvate and uridine. Mitochondria were isolated from 143B TK cells (human bone osteosarcoma, thymidine kinase positive (TK$^+$), mtDNA$^+$, $2*10^6$ cells per well) and incubated with the 143B Rho0 cells. Twenty four hours later, the medium was replaced and the cells were treated with Ganciclovir to eliminate any 143B TK$^+$ cells. The remaining cells were cultured for additional 3 days, and then the medium was replaced with pyruvate and uridine-free medium. After 24 hours, the cells were trypsinized and transferred to 10 cm dish. The medium was replaced every 3 days for the next 9 days. One set of dishes (control and mitochondria-treated) was fixed in methanol and stained with giemsa (FIG. 8A). The second set was trypsinized and assayed for ATP level as an indicator for cell number and mitochondrial activity (FIG. 8B). As seen in FIG. 8B, ATP levels in cells incubated with mitochondria were increased by about 5.3 compared to control.

The results demonstrated in FIG. 8 clearly indicate that isolated, mtDNA$^+$ mitochondria are capable to interact with human bone mtDNA$^-$ cells and increase their survival, proliferation and ATP production.

Example 9. Mitochondria can Enter Human Bone Marrow Cells

Figure 9A:
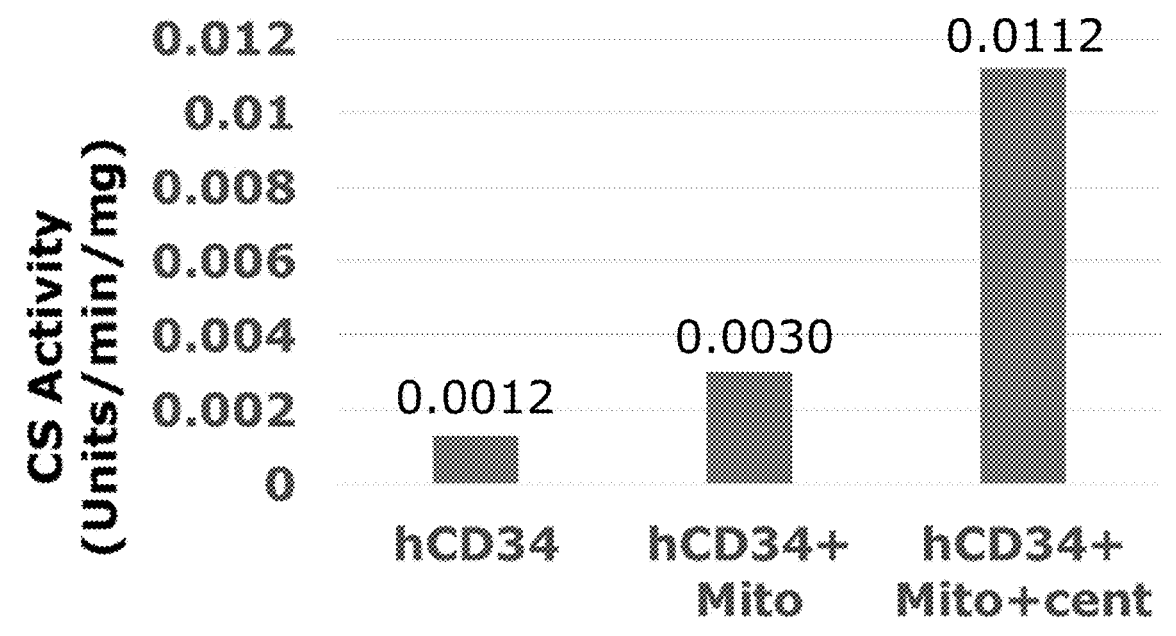
FIG. 9A is a bar graph showing a comparison of CS activity in control, untreated human BM cells and human BM cells incubated with GFP-labeled mitochondria isolated from human placental cells, with or without centrifugation.
Figure 9B:
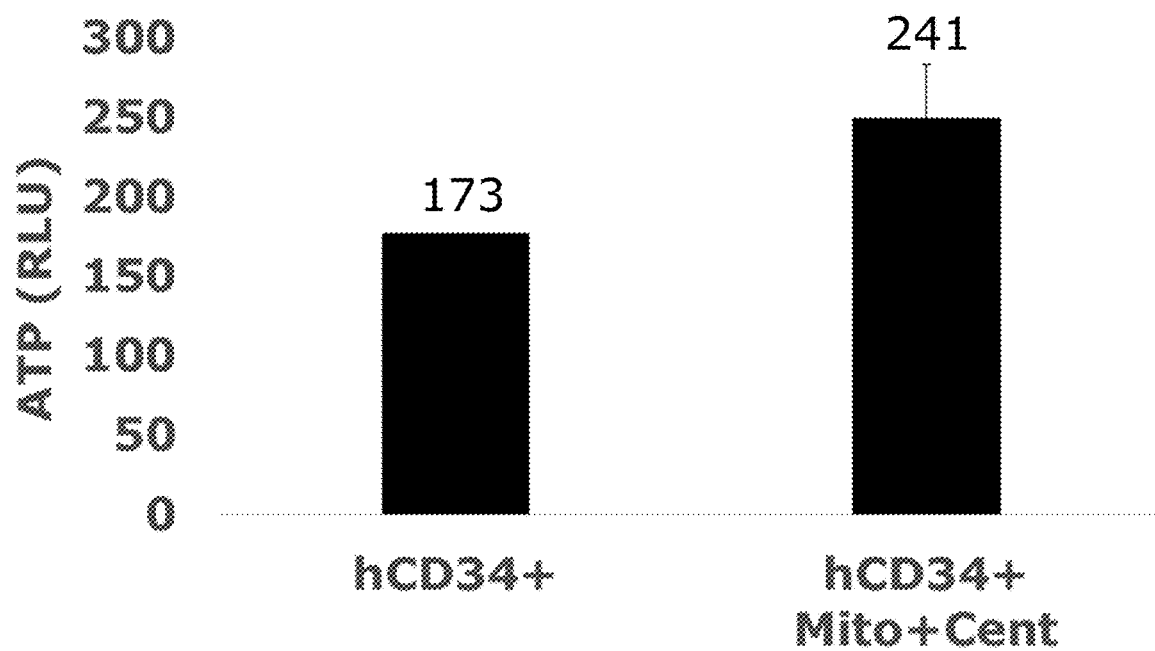
FIG. 9B is a bar graph showing a comparison of ATP levels in control, untreated human BM cells and human BM cells incubated with GFP-labeled mitochondria isolated from human placental cells, with centrifugation.

Human CD34$^+$ cells (1.4*10$^5$, ATCC PCS-800-012) were untreated or incubated for 20 hours with GFP-labeled mitochondria isolated from human placental cells. Before plating the cells, mitochondria were mixed with the cells, centrifuged at 8000 g and re-suspended. After incubation, the cells were washed twice with PBS and CS activity was measured using the CS0720 Sigma kit (FIG. 9A). ATP content was measured using ATPlite (Perkin Elmer) (FIG. 9B). The CS activity levels (FIG. 9A) measured under the conditions specified above are summarized in Table 2.

TABLE 2

|  | (+) Cent | (−) Cent | (+) Cent, normalized | (−) Cent, nor normalized |
|---|---|---|---|---|
| Cells |  | 0.001286445 |  | 1 |
| Cells + Mitochondria |  | 0.003003348 |  | 2.33 |
| Cells + Mitochondria + Centrifugation | 0.011202225 |  | 8.7 |  |

The results demonstrated in FIG. 9 (see Table 2) clearly indicate that the mitochondrial content of human bone-marrow cells may be increased many fold by interaction and co-incubation with isolated human mitochondria, to an extent beyond the capabilities of either human or murine fibroblasts or murine bone-marrow cells.

Figure 10A:
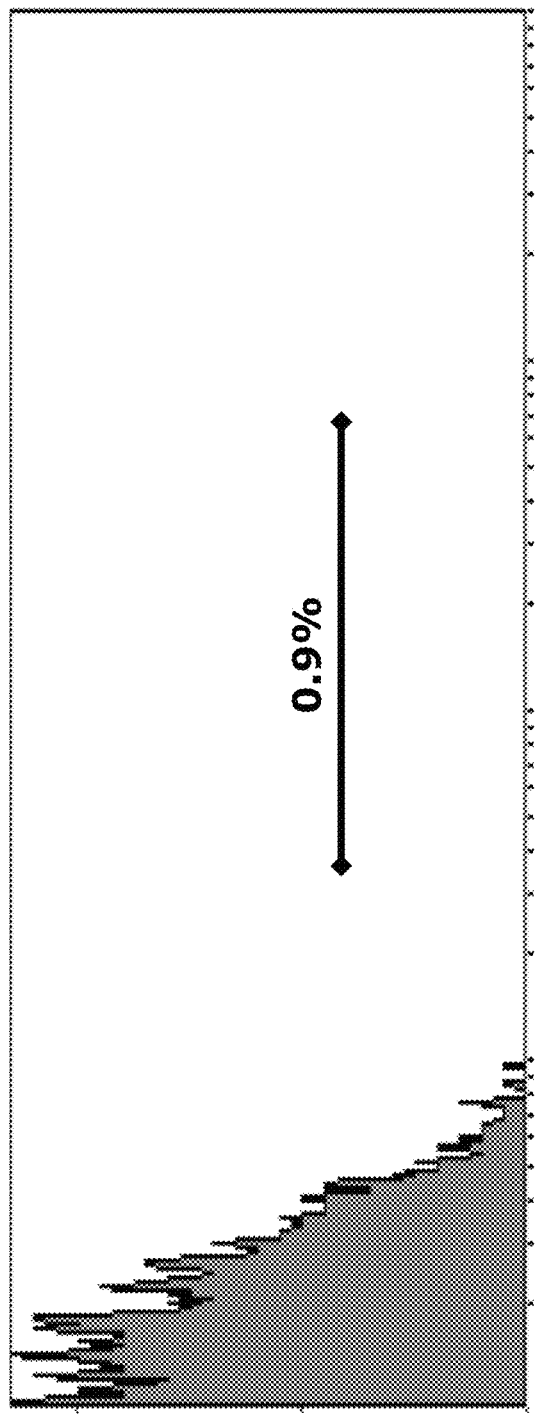
FIG. 10A depict the result of a FACS analysis in human BM cells not incubated with GFP-labeled mitochondria.
Figure 10B:
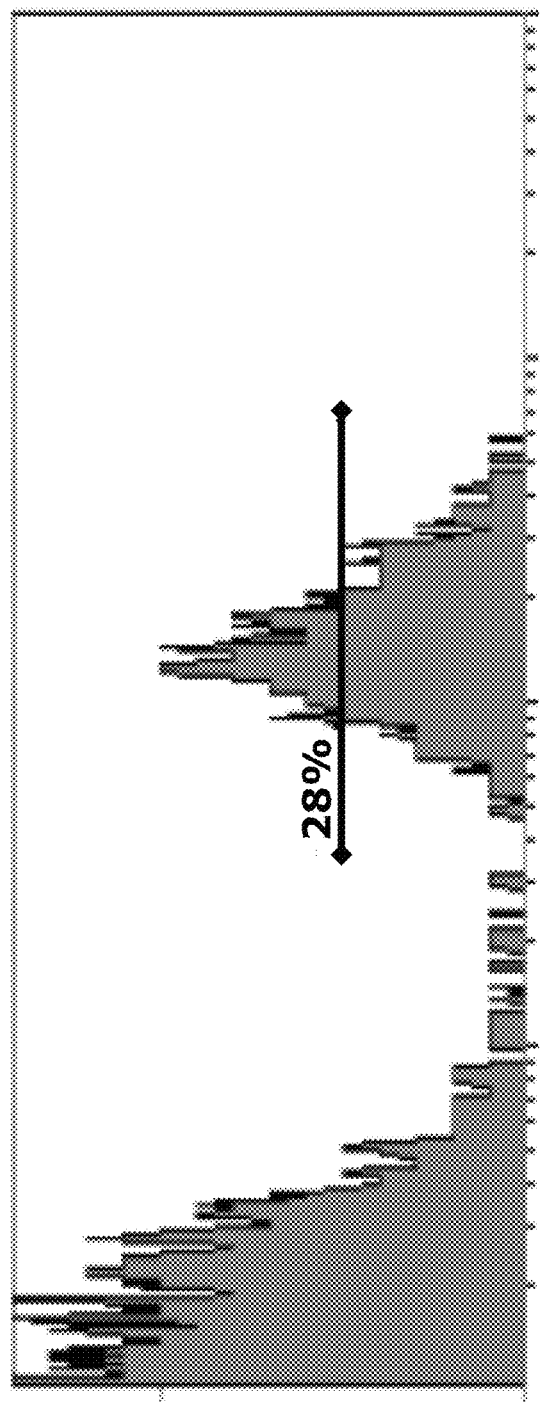
FIG. 10B depict the result of a FACS analysis in human BM cells incubated with GFP-labeled mitochondria after centrifugation.

The cell populations depict in FIG. 9B were further evaluated by FACS analysis. While in the CD34$^+$ cells not incubated with GFP-labeled mitochondria only a minor portion (0.9%) of the cells were fluorescent (FIG. 10A), the CD34$^+$ cells incubated with GFP-labeled mitochondria after centrifugation were substantially fluorescent (28.4%) (FIG. 10B).

Example 10. Mouse Mitochondrial Disease Model

Mouse mitochondria from WT murine placenta are harvested and used to treat bone marrow of the mouse model of mitochondrial disease (such as with a mutation in mtDNA tRNA-Ala). Briefly, diseased bone marrow cells are treated ex-vivo with murine placental mitochondria at different concentrations and incubation times, and injected to another diseased mouse. For comparison, healthy bone marrow transplantation from a healthy mouse to a diseased mouse is also conducted. Assays of efficacy are performed at various time points (before transplantation: ATP level, O$_2$ consumption, citrate synthase (CS) activity; after transplantation: ATP synthesis, O$_2$ consumption, heteroplasmy of mtDNA, CS activity and presence of lactic acid in blood. Biodistribution of mitochondria is tested at 1 day, 1 week, and 1 month after injection by PCR analysis of the mutated vs. wild type mitochondrial tRNA gene in different tissues (mainly bone marrow, heart, skeletal muscle, liver and brain).

Example 11. Human Patient's Fibroblasts Treatment

High-purity active human placental mitochondria grown in 3D cultures are isolated and characterized in terms of CS activity and O$_2$ consumption. Patients with mtDNA mutations or deletions presenting with mitochondrial disease (LHON, MELAS, Leigh syndrome, Pearson's disease, Alper's syndrome) provide fibroblasts isolated from their skin biopsies. Mitochondria augmentation and rescue capabilities are tested both in patient's fibroblasts and in fibroblasts converted in-vitro to induced pluripotent stem (iPS) cells reprogrammed to hematopoietic lineage (to avoid the need in bone marrow aspiration from the patients). The cells are treated with human mitochondria and mtDNA heteroplasmy, CS activity, ATP content and O$_2$ consumption are tested at different time points after incubation with mitochondria (3 hours, 24 hours, and 48 hours).

Example 12. Systemic Bio-Distribution of Bone Marrow Cells Enriched with Mitochondria Mitochondria are introduced into bone marrow cells of control healthy mice from two different backgrounds: the source of mitochondria will be from mice with different mtDNA sequences (Jenuth J P et al., Nature Genetics, 1996, Vol. 14, pages 146-151).

The steps of the method are (1) isolation mitochondria from placenta/livers of Balb/C mice, frozen at −80 and defrosted, or used fresh; (2) bone marrow isolation from e.g. NZB strain; (3) mixing the mitochondria and bone marrow and centrifugation at 8000 g, 5 minutes, resuspending and incubating for 24 hours; (4) washing the bone marrow cells twice with PBS and injecting into a tail vain of a mouse. After 24 hours, a week, a month and 3 months post transplantation tissues (blood, bone marrow, brain, heart, kidney, liver, lung, spleen, skeletal muscle, eye) are collected and DNA is extracted for further sequence analysis.

Example 13. Systemic Therapy by Bone Marrow Cells Enriched with Mitochondria Mitochondria are introduced into bone marrow cells of ND6, a mitochondrial disease mouse model, similar to LHON (Chun Shi Lin et al., PNAS, 2012, Vol. 109(49), pages 20065-20070) to prove that healthy mitochondria may partly rescue the phenotype of ND6 mouse model. The steps of the method are (1) isolation of mitochondria from placenta/livers of B6ME mice (WT strain of the ND6 mouse), frozen at −80 and defrosted, or used fresh; (2) bone marrow isolation from 1A1B6ME mice (ND6 mutant mouse on B6ME background); (3) mixing the mitochondria and bone marrow and centrifugation at 8000 g, 5 minutes, resuspending and incubating for 24 hours; (4) washing the bone marrow cells twice with PBS and injecting into the tail vain of a 1A1B6ME mouse. After 24 hours, a week, a month and 3 months post transplantation tissues (blood, bone marrow, brain, heart, kidney, liver, lung, spleen, skeletal muscle, eye) are collected and DNA is extracted for further sequence analysis. During the entire period, evaluating changes in food consumption, body weight, lactic acidosis, blood counts and biochemical blood markers.

Example 14. Safety and Bio-Distribution Studies

Human blood mitochondria are introduced into mouse bone marrow cells for safety studies and bio-distribution.

The steps of the method are (1) isolation of mitochondria from human white blood cells and platelets, frozen at −80 and defrosted, or used fresh; (2) bone marrow isolation from e.g. C57/bl mice; (3) mixing the mitochondria and bone marrow and centrifugation at 8000 g, 5 minutes, resuspending and incubating for 24 hours; (4) washing the bone marrow cells twice with PBS and injecting into the tail vain of e.g. C57/bl mouse. After 24 hours, a week, a month and 3 months post transplantation tissues (blood, bone marrow, brain, heart, kidney, liver, lung, spleen, skeletal muscle, eye) are collected and DNA is extracted for further sequence analysis. During the entire period, evaluating changes in food consumption, body weight, lactic acidosis, blood counts and biochemical blood markers.

Example 15. Therapy of Human Patients Afflicted by a Mitochondrial Disease

The steps of the method for therapy of human patients afflicted by a mitochondrial disease are (1) administering to a patient afflicted by a mitochondrial disease, for example LHON, MELAS or Pearson Syndrome, G-CSF in a dosage of 10-16 µg/kg for 5 days; (2) on day 6, performing apheresis on the blood of the patient to obtain bone marrow cells; (3) in parallel, isolating functional mitochondria from a blood sample of a healthy donor; (4) incubation of bone marrow cells with functional mitochondria for 24 hours; (5) washing the bone marrow cells; and (6) infusion of bone marrow cells loaded with mitochondria to the patient. During the entire period, evaluating changes in the patient's food consumption, body weight, lactic acidosis, blood counts and biochemical blood markers.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An ex-vivo method for enriching human $CD34^+$ bone-marrow cells with mitochondria, comprising:
   (i) providing a first composition, comprising a plurality of intact human $CD34^+$ bone-marrow cells obtained or derived from a patient afflicted with a mitochondrial disease or from a subject not afflicted with a mitochondrial disease;
   (ii) providing a second composition, comprising a plurality of isolated intact functional human mitochondria obtained from a subject not afflicted with a mitochondrial disease;
   (iii) co-incubating the human $CD34^+$ bone-marrow cells of the first composition with the isolated intact functional human mitochondria of the second composition, thus forming a third composition; and
   (iv) incubating the third composition under conditions allowing the human mitochondria to enter the human $CD34^+$ bone-marrow cells thereby enriching said human $CD34^+$ bone-marrow cells with said human intact functional mitochondria, thus forming a fourth composition;
wherein the mitochondrial content of the human $CD34^+$ bone-marrow cells in the fourth composition is higher than the mitochondrial content of the human $CD34^+$ bone-marrow cells in the first composition.

2. The method of claim 1, further comprising determining the content or activity level of citrate synthase in the first composition and the fourth composition.

3. The method of claim 1, wherein the bone-marrow cells in the first composition are mobilized from the bone marrow of the patient or the subject.

4. The method of claim 1, further comprising concentrating the human $CD34^+$ bone-marrow cells and the mitochondria in the third composition before or during incubation.

5. The method of claim 4, further comprising centrifugation of the third composition before, during or after incubation.

6. The method of claim 1, wherein the human $CD34^+$ bone-marrow cells in the first composition are obtained from a patient afflicted with a mitochondrial disease, and have:
   (i) a sub-normal rate of oxygen (O2) consumption;
   (ii) a sub-normal content or activity level of citrate synthase;
   (iii) a sub-normal rate of adenosine triphosphate (ATP) production; or
   (iv) any combination of (i), (ii) and (iii).

7. The method of claim 6, wherein the heteroplasmy level of the bone-marrow cells in the fourth composition is at least 50% lower than the heteroplasmy level of the bone-marrow cells in the first composition.

8. The method of claim 1, wherein the human $CD34^+$ bone-marrow cells in the first composition are obtained from a subject not afflicted with a mitochondrial disease, and have:
   (i) a normal rate of oxygen (O2) consumption;
   (ii) a normal content or activity level of citrate synthase;
   (iii) a normal rate of adenosine triphosphate (ATP) production; or
   (iv) any combination of (i), (ii) and (iii).

9. The method of claim 1, wherein the isolated human mitochondria in the second composition are obtained from a subject not afflicted with a mitochondrial disease, and have:
   (i) a normal rate of oxygen (O2) consumption;
   (ii) a normal content or activity level of citrate synthase;
   (iii) a normal rate of adenosine triphosphate (ATP) production; or
   (iv) any combination of (i), (ii) and (iii).

10. The method of claim 1, further comprising measuring the total amount of mitochondrial proteins in the second composition, wherein the total amount is between 20%-80% of the total amount of cellular proteins within the composition.

11. The method of claim 1, comprising measuring the fourth composition for cytochrome C reductase or cytochrome C reductase activity, wherein cytochrome C reductase or cytochrome C reductase activity is not enriched as compared to the first composition.

12. The method of claim 1, wherein the mitochondrial disease is a mitochondrial respiratory chain disease (MRCD).

13. The method of claim 1, wherein the mitochondrial disease is selected from the group consisting of LHON (Leber's hereditary optic neuropathy); MELAS (mitochondrial myopathy, encephalomyopathy, lactic acidosis, stroke-like symptoms); Pearson syndrome; Leigh syndrome; NARP (neuropathy, ataxia, retinitis pigmentosa, and ptosis); MERRF (myoclonic epilepsy with ragged red fibers); KSS (Kearns-Sayre Syndrome); MNGIE (myoneurogenic gastrointestinal encephalopathy); Friedreich Ataxia; and Alpers' disease.

14. The method of claim 13, wherein the mitochondrial disease is selected from the group consisting of LHON, MELAS, Pearson syndrome, Leigh syndrome, NARP, MERRF, and KSS.

* * * * *